United States Patent
KenKnight et al.

(10) Patent No.: US 8,442,631 B2
(45) Date of Patent: May 14, 2013

(54) SYSTEM AND METHOD FOR DETERMINING THE ORIGIN OF A SENSED BEAT

(75) Inventors: Bruce KenKnight, Maple Grove, MN (US); Steven D. Girouard, Chagrin Falls, OH (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 119 days.

(21) Appl. No.: 11/745,667

(22) Filed: May 8, 2007

(65) Prior Publication Data

US 2008/0281369 A1 Nov. 13, 2008

(51) Int. Cl.
*A61N 1/36* (2006.01)

(52) U.S. Cl.
USPC .................. 607/9; 600/509; 600/510; 607/2; 607/3

(58) Field of Classification Search .......... 600/509–510; 607/2–3, 9
See application file for complete search history.

(56) References Cited

U.S. PATENT DOCUMENTS

| | | |
|---|---|---|
| 5,240,009 A | 8/1993 | Williams |
| 5,273,049 A | 12/1993 | Steinhaus et al. |
| 5,280,792 A | 1/1994 | Leong et al. |
| 5,400,795 A | 3/1995 | Murphy et al. |
| 5,645,070 A | 7/1997 | Turcott |
| 5,682,900 A | 11/1997 | Arand et al. |
| 5,779,645 A | 7/1998 | Olson et al. |
| 5,817,133 A | 10/1998 | Houben |
| 5,819,741 A | 10/1998 | Karlsson et al. |
| 5,857,977 A | 1/1999 | Caswell et al. |
| 5,859,922 A | 1/1999 | Hoffmann |
| 5,944,743 A | 8/1999 | Janssens |
| 6,076,014 A | 6/2000 | Alt |
| 6,223,078 B1 | 4/2001 | Marcovecchio |
| 6,266,554 B1 | 7/2001 | Hsu et al. |
| 6,275,732 B1 | 8/2001 | Hsu et al. |
| 6,308,095 B1 | 10/2001 | Hsu et al. |
| 6,312,388 B1 | 11/2001 | Marcovecchio et al. |
| 6,434,417 B1 | 8/2002 | Lovett |
| 6,449,503 B1 | 9/2002 | Hsu |
| 6,650,937 B2 | 11/2003 | Kerver |

(Continued)

FOREIGN PATENT DOCUMENTS

| | | |
|---|---|---|
| WO | WO 00/47278 | 8/2000 |
| WO | WO 02/05893 A1 | 1/2002 |

OTHER PUBLICATIONS

Bucchi et al., "Wild-Type and Mutant HCN Channels in a Tandem Biological-Electronic Cardiac Pacemaker," *Circulation*, 114(10): 992-999 (2006).

(Continued)

*Primary Examiner* — Carl H Layno
*Assistant Examiner* — Jennifer Ghand
(74) *Attorney, Agent, or Firm* — Pauly, Devries Smith & Deffner, L.L.C.

(57) ABSTRACT

A method for monitoring a biological cardiac pacemaker. The method may include stimulating a heart at a region selected for implantation of a biological pacemaker and sensing at least one electrical signal indicative of a cardiac depolarization originating in the region selected for implantation of the biological pacemaker. The method may further include sensing at least one subsequent electrical signal produced by the heart and determining if the subsequent electrical signal originated in the region selected for the biological pacemaker or another region of the heart.

15 Claims, 10 Drawing Sheets

U.S. PATENT DOCUMENTS

| | | | |
|---|---|---|---|
| 6,671,558 | B1 | 12/2003 | Soykan et al. |
| 6,775,574 | B1 | 8/2004 | Soykan et al. |
| 6,959,212 | B2 | 10/2005 | Hsu et al. |
| 7,146,213 | B1 * | 12/2006 | Levine ............... 607/9 |
| 2002/0019593 | A1 * | 2/2002 | Hsu et al. ............ 600/513 |
| 2002/0183637 | A1 | 12/2002 | Kim et al. |
| 2003/0060851 | A1 | 3/2003 | Kramer et al. |
| 2003/0195572 | A1 * | 10/2003 | Bocek et al. ............ 607/9 |
| 2003/0211088 | A1 * | 11/2003 | Field ............... 424/93.21 |
| 2004/0137621 | A1 | 7/2004 | Rosen et al. |
| 2004/0215251 | A1 | 10/2004 | Sharma et al. |
| 2004/0254134 | A1 | 12/2004 | Marban et al. |
| 2005/0002914 | A1 | 1/2005 | Rosen et al. |
| 2005/0021089 | A1 | 1/2005 | Sharma |
| 2005/0021091 | A1 * | 1/2005 | Laske et al. ............ 607/3 |
| 2005/0043652 | A1 | 2/2005 | Lovett et al. |
| 2005/0192506 | A1 | 9/2005 | Kim et al. |
| 2005/0192637 | A1 | 9/2005 | Girouard et al. |
| 2005/0283196 | A1 * | 12/2005 | Bocek et al. ............ 607/9 |
| 2005/0288721 | A1 | 12/2005 | Girouard et al. |
| 2006/0009812 | A1 | 1/2006 | Daum et al. |
| 2006/0015146 | A1 | 1/2006 | Girouard et al. |
| 2008/0103536 | A1 * | 5/2008 | Xiao ..................... 607/3 |
| 2008/0103537 | A1 * | 5/2008 | Sigg et al. ............. 607/3 |
| 2009/0053180 | A1 * | 2/2009 | Rosen et al. ........ 424/93.7 |

OTHER PUBLICATIONS

Cohen, et al., "The Why, What, How and When of Biological Pacemakers," *Nature Clinical Practice*, 2(8): 374-375 (2005).

Gepstein, "Stem Cells as Biological Heart Pacemakers," *Expert Opin. Biol. Ther*. 5(12): 1531-1537 (2005).

Kehat et al., "Electromechanical Integration of Cardiomyocytes Derived from Human Embryonic Stem Cells," *Nature Biotechnology*, 22(10): 1282-1289 (2004).

Plotnikov et al., "Biological Pacemaker Implanted in Canine Left Bundle Branch Provides Ventricular Escape Rhythms That Have Physiologically Acceptable Rates," *Circulation*, 109(4): 506-512 (2004).

Plotnikov et al., "Tandem Biological/Electronic Pacing Increases Versatility over Electronic Pacing Alone While Maintaining Safety," Heart Rhythm Society 27th Annual Scientific Sessions, Abstracts (2006).

Potapova et al., "Human Mesenchymal Stem Cells as a Gene Delivery System to Create Cardiac Pacemakers," *Circulation Research*, 94(7): 952-959 (2004).

Rosen et al., "Genes, Stem Cells and Biological Pacemakers," *Cardiovascular Research*, 64: 12-23 (2004).

Rosen, "Biological Pacemaking: In Our Lifetime?" *Heart Rhythm* 2(4): 418-428 (2005).

Qu et al., "Expression and Function of a Biological Pacemaker in Canine Heart," *Circulation*, 107(8): 1106-1109 (2003).

International Search Report for International Application No. PCT/US2008/058271, mailed Aug. 27, 2008.

Written Opinion of the International Searching Authority for International Application No. PCT/US2008/058271, mailed Aug. 27, 2008.

\* cited by examiner

SYSTEM AND METHOD FOR DETERMINING THE ORIGIN OF A SENSED BEAT

FIELD OF THE INVENTION

The present invention relates to devices and methods for determining the origin of a sensed cardiac signal. The system and method may be used in conjunction with implantable cardiac pacemakers.

BACKGROUND OF THE INVENTION

The heart is a muscular organ that pumps blood throughout the body. In a normal, healthy heart the pumping is initiated by periodic electrical depolarizations, which originate in the sinoatrial node. The electrical depolarizations spread throughout the myocardium, causing the heart to contract, forcing blood into the aorta and pulmonary artery.

In healthy hearts, the myocardial depolarization occurs in a coordinated sequence, which facilitates adequate pumping. As noted, the initial depolarization generally originates in the sinoatrial node and spreads throughout the atria, thereby causing the atria to contract, forcing blood into the ventricles. Subsequently, the depolarization passes through the atrioventricular node and, through a group of specialized conducting myocardial fibers (Purkinje fibers), is transmitted through the interventricular septum and ventricles. The left and right ventricles are thus depolarized and contract to pump blood through the pulmonary artery and aorta to the body.

Heart disease is a major health problem. Numerous environmental, behavioral, genetic, and/or congenital conditions can lead to chronic or acute damage to the heart. Acute myocardial events, such as a myocardial infarction, may damage portions of the heart's native pacemakers (i.e. sinoatrial and atrioventricular nodes) or conduction systems, and may decrease the overall pumping effectiveness of the heart. Likewise, chronic conditions, such as high blood pressure, valvular disease, certain types of infection, and diabetes, may produce slowly-progressing, but similarly damaging effects on the heart.

One way to treat damaged heart muscle cells is to provide pharmaceutical therapies in an effort to restore heart function. Many pharmacologic treatments are effective at improving patient quality of life by increasing cardiac output, preventing arrhythmias, and/or treating symptoms associated with heart failure. However, for some patients, pharmaceutical therapy may be ineffective or inadequate. For example, many patients who have suffered acute or chronic damage to the heart's pacemakers or conduction systems have lasting and/or recurring arrhythmias. In addition, in some patients, conduction through the ventricles may be abnormal and/or the depolarizations may be asynchronous, whereby contractions of the atria and ventricles are poorly coordinated. Further, many patients have difficulties complying with pharmaceutical regimens. All these conditions may have a deleterious effect on cardiac output, may contribute to the progression of cardiac disease, and may ultimately lead to death.

For many patients, implantable cardiac rhythm management systems (e.g. pacemakers, cardiac resynchronization pacemakers and/or defibrillators) are necessary. Pacemakers generally include a housing (can) that encloses various electrical components, such as a battery, control hardware, communications systems, and/or other diagnostic components. The pacemaker also includes a number of leads and electrodes, which interface with portions of the heart to be stimulated. Numerous different pacemakers and/or defibrillators are available, and the specific type of device is selected based on a variety of clinical factors that are evaluated by a physician.

More recently, there has been growing interest in developing pacemakers using cellular sources, which may be implanted or injected into certain regions of the heart to produce a new, biological pacemaker. The cells may be engineered to have electrical properties that mimic natural cardiac pacemakers, but may be implanted at a variety of cardiac locations and may be selected based on particular patient needs. However, the use of biological pacemakers may present some limitations, and even with a biological pacemaker, many patients may still benefit from an implantable device. For example, the biological pacemaker may have inherent limits on cardiac rates that it can achieve, and an implantable device may be needed when higher metabolic demands are encountered. Further, a biological pacemaker may be temporarily or permanently affected by medications or any condition that may affect normal myocardial cells (e.g. infarction). In addition, an implantable device may be desired to monitor, record, and/or transmit information related to patient status, including biological pacemaker status, to healthcare professionals to facilitate continued treatment.

For some biological pacemakers, the biological pacemaker may not begin to function as desired until some time after implantation. During this time, an implantable electrical pacemaker may be used. However, as the biological pacemaker begins to function, it would be useful to determine if sensed cardiac depolarizations originate in the implantable electrical pacemaker, in the biological pacemaker, in an ectopic cardiac site, or in the native pacemaker. The present inventors have discovered that this information can be used to determine how the implantable electrical pacemaker should operate and how well the biological pacemaker is functioning.

The present disclosure provides systems and methods for determining the origin of a sensed cardiac electrical signal.

SUMMARY OF THE INVENTION

A first aspect of the present disclosure includes a method for monitoring a biological cardiac pacemaker. The method may include stimulating a heart at a region selected for implantation of a biological pacemaker and sensing at least one cardiac complex indicative of a cardiac depolarization originating in the region selected for implantation of the biological pacemaker. The method may further include sensing at least one subsequent cardiac complex produced by the heart and determining if the subsequent cardiac complex originated in the region selected for the biological pacemaker or another region of the heart. Based on this determination, the performance of the biological pacemaker may be assessed, and cardiac therapies may be controlled to improve overall cardiac performance.

A second aspect of the present disclosure includes an implantable medical device for monitoring an implanted biologic pacemaker. The device may comprise a first sensing system for detecting a cardiac signal at a first location and a second sensing system for detecting a cardiac signal at a second location. The device may further include a processor unit configured to compare information derived from sensed cardiac signals from the first sensing system and second sensing system with at least one template cardiac signal to determine if the sensed cardiac signals originated in the location of a biologic cardiac pacemaker.

A third aspect of the present disclosure includes a method for monitoring a biological cardiac pacemaker. The method may comprise implanting a biologic pacemaker in a ventricle of a heart; monitoring two or more cardiac signals representative of cardiac depolarization; and detecting a cardiac complex in each of the two or more cardiac signals during a depolarization originating in a supraventricular location. A template time difference between two repeatably identifiable features on at least one of the two or more cardiac signals may be determined. The method may further include detecting at least one additional cardiac complex in each of the two or more cardiac signals subsequent to implantation of the biological pacemaker and determining a second time difference between two repeatably identifiable features on at least one of the additional cardiac complexes. Finally, the method may include determining if the subsequent cardiac complex originated in the region selected for the ventricular biological pacemaker or another region of the heart.

A fourth aspect of the present disclosure includes a method for monitoring a biological cardiac pacemaker. The method may comprise monitoring a first signal and a second signal representative of electrical cardiac activity. The method may further include detecting a normal sinus rhythm (NSR) cardiac complex in each of the first signal and the second signal and detecting at least one additional cardiac complex in each of the first signal and the second signal. A predetermined feature may be determined in the cardiac complex detected in the first signal and a first NSR representative complex. The predetermined feature may includes a repeatably identifiable complex section common to the cardiac complex detected in the first signal and the first NSR representative complex. The predetermined feature in the at least one additional cardiac complex detected in the first signal and the first NSR representative complex may be aligned, and the cardiac complex detected in the second signal may be compared to a second NSR representative complex. Finally, the at least one additional cardiac complex may be classified as a ventricular biologic pacemaker complex based on the comparison of the morphology of the cardiac complex in the second cardiac signal to the second NSR representative complex.

A fifth aspect of the present disclosure includes a method for monitoring an implanted biological pacemaker. The method may comprise monitoring a first cardiac signal and a second cardiac signal and detecting a cardiac complex in each of the first cardiac signal and the second cardiac signal. The morphology of the cardiac complex in the first cardiac signal may be compared to a first template morphology and the morphology of the cardiac complex in the second cardiac signal may be compared to a second template morphology. The cardiac complex may be classified as either originating in a biological pacemaker or another cardiac location based on the comparison of the morphology of the cardiac complex in the first cardiac signal and the second cardiac signal to the first template morphology and the second template morphology.

A sixth aspect of the present disclosure includes a system for monitoring an implanted biological pacemaker. The method may include at least one cardiac lead having at least a first cardiac electrode and a second cardiac electrode. The system may further include a sensing system attached to the first cardiac electrode and the second cardiac electrode, wherein the sensing system senses a first signal and a second signal representative of cardiac electrical activity. The system may also include a morphology analyzer circuit coupled to the sensing system, wherein the morphology analyzer circuit locates a position of at least one predetermined feature in the morphology of the cardiac complex in the first signal and the second signal and generates two or more scalar values as a function of the position of the at least one predetermined feature for each of the first signal and the second signal. In addition, the system may include a template generator coupled to the morphology analyzer, wherein the template generator circuit creates a cardiac complex vector from the two or more scalar values generated by the morphology analyzer circuit. Finally the system may include a signal feature comparison circuit coupled to the morphology analyzer circuit and the template generator circuit, wherein the signal feature comparison circuit compares the cardiac complex vector to one or more classification vectors to determine if the a sensed cardiac complex originated in a ventricular biological pacemaker.

A seventh aspect of the present disclosure includes a system for monitoring an implanted biological pacemaker. The system may comprise at least one cardiac lead having at least a first cardiac electrode and a second cardiac electrode. The system may further include a sensing system attached to the first cardiac electrode and the second cardiac electrode, wherein the sensing system senses a first signal and a second signal representative of electrical cardiac activity. The system may also include a template generator circuit coupled to the sensing system, wherein the template generator circuit determines a first NSR representative complex and a second NSR representative complex from a plurality of cardiac complexes sensed during normal sinus rhythm. In addition, the system may include a morphology analyzer circuit coupled to the sensing system, wherein the morphology analyzer circuit locates a predetermined feature in a cardiac complex detected in the first signal and in the first NSR representative complex and the predetermined feature includes a repeatably identifiable complex section common to the cardiac complex detected in the first signal and the first NSR representative complex. Finally, the system may include a signal feature comparison circuit coupled to the morphology analyzer circuit and the template generator circuit, wherein the signal feature comparison circuit aligns the predetermined feature in the cardiac complex monitored in the first signal with the predetermined feature on the first NSR representative complex and compares the cardiac complex monitored in the second signal to the second NSR representative complex to determine whether the cardiac complex originated in a ventricular biological pacemaker.

It is to be understood that both the foregoing general description and the following detailed description are exemplary and explanatory only, and are not restrictive of the invention, as claimed.

The accompanying drawings, which are incorporated in and constitute a part of this specification, illustrate several embodiments of the invention and together with the description, serve to explain the principles of the invention.

Additional objects and advantages of the invention will be set forth in part in the description which follows or may be learned by practice of the invention. The objects and advantages of the invention will be realized and attained by means of the elements and combinations particularly pointed out in the appended claims.

DESCRIPTION OF EXEMPLARY EMBODIMENTS

Figure 1:
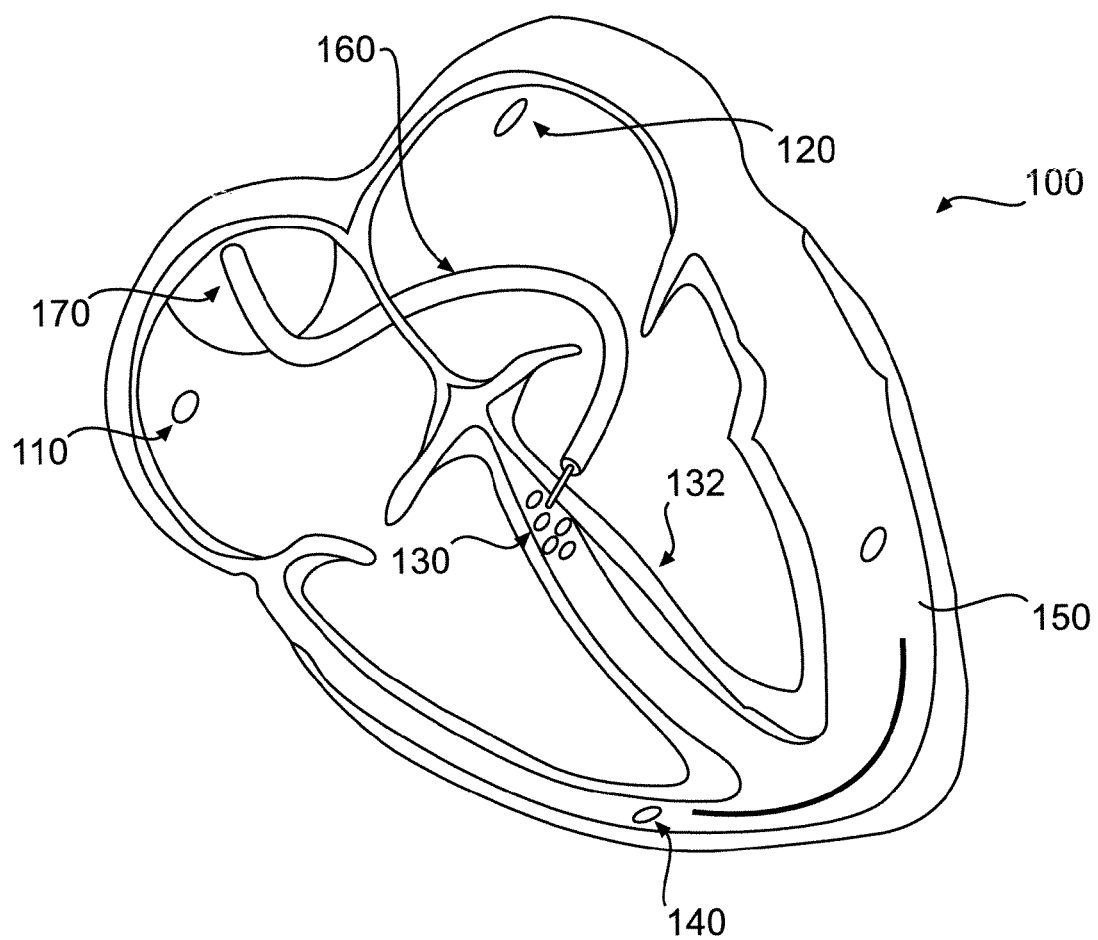
FIG. 1 illustrates a heart including implanted biological pacemakers, according to an exemplary disclosed embodiment.

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents. Throughout the description the term 'biological pacemaker' will be understand to refer to a pacemaker comprising living cells that are implanted, injected, or otherwise placed into the body for electrical stimulation of cardiac tissue. Further, the terms 'pacemaker,' 'implantable device,' 'implantable pacemaker,' 'pacemaker/defibrillator', 'cardioverter', 'cardiac resynchronization pacemaker', and 'pacemaker/ICD' will be understood to refer to a pacemaker, defibrillator, pacemaker/defibrillator combination, or any other implantable device comprising electrical circuits comprising non-living materials. It should also be noted that the examples and cardiac complexes presented here are representative, and are not actual cardiac complex or vectors recorded from patients.

The present disclosure pertains to devices and methods for determining the origin of a sensed cardiac electrical signal. The systems and methods of the present disclosure will provide tools for evaluating the performance of biological pacemakers. In some embodiments, the systems and methods of the present disclosure may be used to determine if a biological pacemaker has begun functioning or is functioning properly after implantation. In other embodiments, the system and/or methods of the present disclosure may be used to periodically or continuously assess the continued viability and/or performance of a biological pacer, and/or to augment the performance of the biological pacemaker.

As described in detail below, the system and methods of the present disclosure may include one or more sensors or electrodes configured to detect and/or measure cardiac electrical depolarizations. Suitable sensors or electrodes may be integrated with an implantable medical device such as a pacemaker, implantable cardioverter-defibrillator (ICD), or pacemaker/ICD. Alternatively, the implantable medical device may be dedicated to monitoring and/or recording electrical signals to assess the performance of an implanted biological pacemaker. In other embodiments, the sensors or electrodes may be located externally (e.g. on a Holter monitor, cardiac telemetry system, or EKG system).

The methods of the present disclosure may include comparing information pertaining to sensed cardiac electrical signals to information pertaining to one or more template electrical signals to determine if a cardiac depolarization originates in the location of a biological pacemaker, in a native cardiac nodal site, in an implantable pacemaker electrode site, or in another cardiac site. As described in detail below, a number of feature comparison techniques may be used to determine the origin of a sensed cardiac electrical signal. In some embodiments, a signal vector may be determined and compared to a template signal vector. In other embodiments, repeatably identifiable points, intervals, or features may be evaluated to make a morphology comparison between one or more template cardiac signals and subsequently-sensed cardiac signals. In other embodiments, a comparison may be made between features identified on near-field and far-field signals for a normal sinus rhythm template with features identified on near-field and far-field signals for subsequently-sensed cardiac complexes. Based on the comparison, the systems and methods of the present disclosure may be used to determine if a subsequently-sensed cardiac complex originates in a left ventricular biological pacemaker, or in another cardiac location.

Conventional implantable pacemakers/defibrillators require a pulse generator comprising a battery and electrical circuits configured to stimulate cardiac sites to effect depolarization and contraction. Unlike conventional pacemakers, biological pacemakers are comprised of living cells or tissue that may be implanted or otherwise grafted in or around the heart. The cells or tissue may be selected and/or produced to provide periodic electric stimulation, much like the pacemaker cells of the heart's sinoatrial or atrioventricular nodes. Various aspects of biological pacemakers are described in Rosen et al, "Genes, stem cells, and biological pacemaker," Cardiovascular Research vol. 64: 12-23 (2004); Gepstein, Lior, "Stem cells as biological pacemakers," Expert Opin. Biol. Ther. vol. 5(12): 1531-1536 (2005); and U.S. Patent Publication 2004/0254134 to Marban et al., all of which are hereby incorporated by reference in their entirety.

Biological pacemakers may be produced from a variety of suitable cellular or tissue sources. For example, biological pacemakers may be produced from pluripotent cell lines, which may be treated and/or genetically altered to produce desired electrical properties. Suitable cell lines may include, but are not limited to, peripheral blood stem cells, bone-marrow derived stem cells, cardiac myoblasts, skeletal myoblasts, embryonic stem cells, adult mesenchymal stem cells, or any other cellular source that may be treated, conditioned, or engineered to produce periodic electrical depolarizations. Further, suitable cell or tissue sources, may include autologous, allogeneic, or xenogeneic sources. Any suitable cellular source may be selected.

As noted, the cells or tissue used for the biological pacemaker may be selected, treated, conditioned, or genetically engineered to produce desired properties. For example, the cells or tissues may be selected or engineered to express certain genes that will provide desired electrical properties.

Such genes may include various ion channels selected to produce periodic electric depolarizations and repolarizations. Other genes may be selected to facilitate formation of gap junctions between cells or tissue to be used as a biological pacemaker and the surrounding myocardium. Further, genes may be selected to provide desired responses to metabolic or hormonal changes, or to pharmaceuticals. In addition, genes may be selected to enhance cell viability or enhance engraftment after implantation.

Cells or tissue selected for the biological pacemakers may be treated prior to or after implantation to enhance their function or encourage differentiation into cardiomyocytes or cardiomyocyte-like cells having desired electrical properties. For example, selected stem cells may be pre-treated ex-vivo to encourage differentiation into cardiomyocytes or to stimulate formation of gap junctions. Further, prior to implantation, selected cells or tissue may be mixed with other materials that may facilitate implantation or enhance engraftment or viability. For example, the cells or tissue may be mixed with selected culture media, extracellular matrix materials, pharmaceuticals, agents selected to control gene expression, antibiotics, and/or any other suitable material.

Selected biological pacemakers may be implanted at a number of suitable cardiac locations. The specific location may be selected based on patient-specific clinical factors that are assessed by a physician. Further, some patients may have biological pacemakers implanted at more than one location. FIG. 1 illustrates a heart 100 with biological pacemakers illustrated at several different locations. It should be understood that the illustrated biological pacemakers of FIG. 1 are provided to indicate where the pacemakers may be implanted, but the location and number of biological pacemakers may vary. For example, some patients may have only one biological pacemaker, but other patients may have several.

As shown, biological pacemakers may be implanted within the interventricular septum, within the atria, or at various locations within the right ventricle or left ventricle. For some patients a right atrial biological pacemaker 110 may be selected to mimic pacing from the SA node. In other patients a left atrial biological pacemaker 120 may be selected with or without a right atrial biological pacemaker 110. In other patients, an interventricular septum biological pacemaker 130 may be selected. For such patients, the pacemaker may be implanted at any location within the septum 132, including for example, near the AV node or more inferiorly near the apex. Further, a right ventricular biological pacemaker 140 or left ventricular biological pacemaker 150 may be used, and any suitable ventricular location may be selected. As noted previously, some patients may have more than one biological pacemaker, including combinations of atrial, ventricular, or septal pacemakers.

Suitable biological pacemakers may be implanted using a variety of techniques. For example, a catheter 160 may be passed into the heart through the superior vena cava 170 or inferior vena cava (not shown), and the catheter 160 may be advanced to the desired implantation site. As shown in FIG. 1, to implant an interventricular biological pacemaker 130 or left ventricular biological pacemaker 150, the catheter 160 may be passed through the interatrial septum, and the pacemaker cells or tissue may be injected at the selected location using a needle or other instrument. Further, the biological pacemaker may be implanted during the implantation procedure for an implantable conventional pacemaker and/or ICD. In some embodiments, the implantable pacemaker may be implanted, and optionally function conventionally, prior to implantation of the biological pacemaker. After implantation of the implantable pacemaker, template waveforms representing cardiac depolarizations originating at the site of the biological pacemaker may be produced by stimulating the myocardium at the location of the biological pacemaker (e.g. using a stimulating lead on the catheter 160). Further, the implantable pacemaker may be used to sense and store signals representative of the template waveforms, and perform other monitoring or support functions as necessary.

Figure 2:
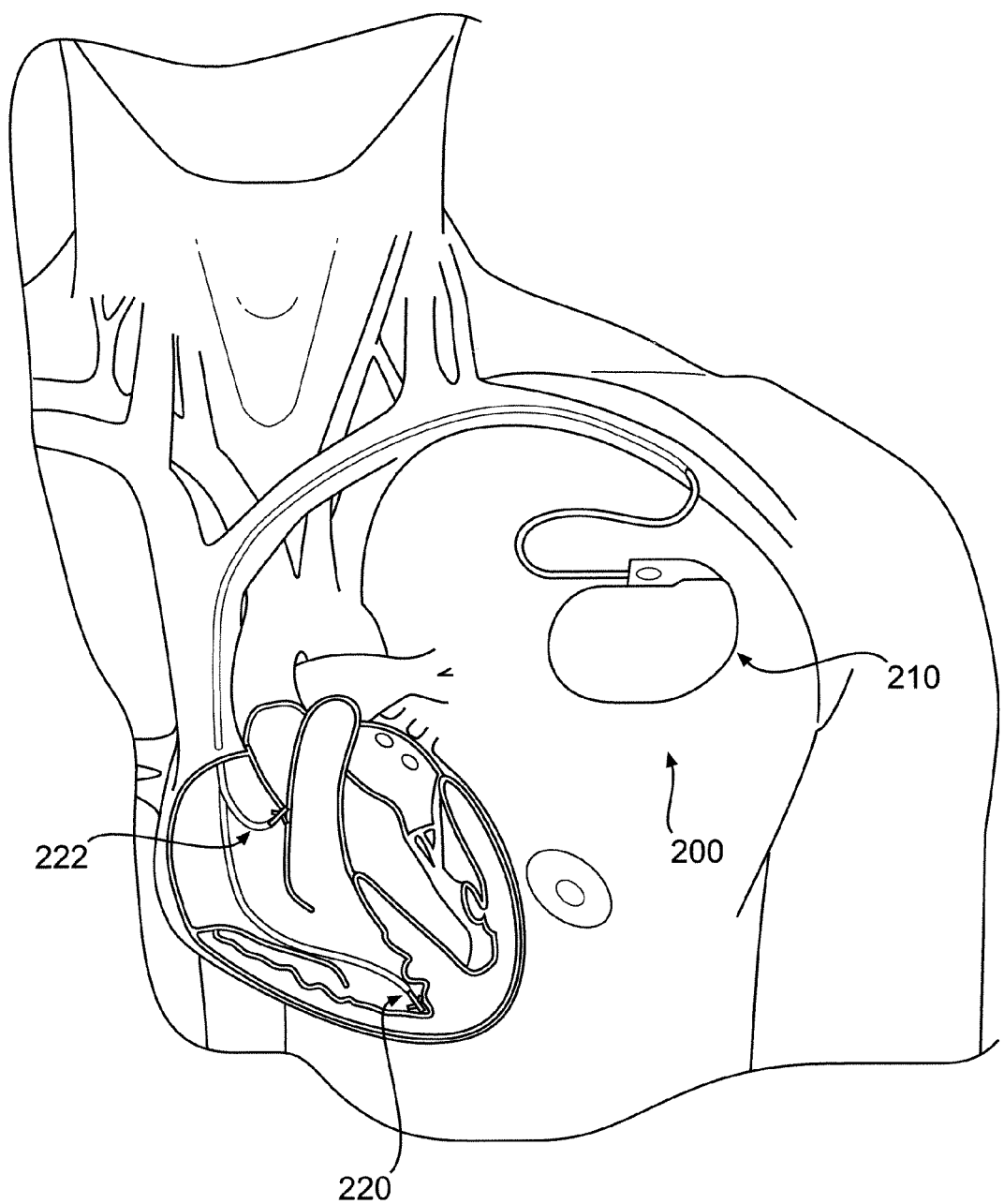
FIG. 2 illustrates a pacemaker implanted in a patient, according to an exemplary disclosed embodiment.

FIG. 2 illustrates an exemplary embodiment of a pacemaker 200 that may be implanted in conjunction with a biological pacemaker. As shown, the pacemaker 200 includes a pulse generator (can) 210 implanted in a subclavian site. Two right heart leads 220, 222 are connected to the pulse generator 210 and fed into the heart through the superior vena cava. First lead 220 is configured to stimulate the right ventricle, and second lead 222 is configured to stimulate the right atrium.

It should be noted that a variety of different lead configurations may be selected. For example, as shown two right-heart leads 220, 222 are provided. However, any suitable number of leads may be selected. For example, one or more left heart leads may be provided through one or more coronary veins. In addition, any suitable lead types may be selected, including, for example, epicardial leads, subcutaneous leads, and/or intravascular leads. Further, the leads may include sensing and/or stimulating electrodes, may include unipolar leads, bipolar leads or any other lead polarity, may include defibrillation electrodes, patch electrodes, and may include any other desired sensors, including for example, pressure, chemical, or gas sensors. Any suitable lead and/or electrode design may be selected.

The pacemaker 200 may be configured to provide any pacing or defibrillation therapy as is known in the art. For example, any desired pacing mode (e.g. VDD, AAI, DDDR) or therapy (e.g. cardiac resynch therapy, post-MI therapies, and/or angiogenic stimulation) may be selected based on patient-specific characteristics. Further, the pacemaker 200 may be configured to function only during inadequate pacing by an implanted biological pacemaker or native pacemaker. Alternatively, the pacemaker 200 may be configured to provide pacing therapy immediately following implantation of the biological pacemaker until the biological pacemaker has become engrafted and functions properly. In other embodiments, the pacemaker 200 may be configured to continuously or periodically evaluate the performance of one or more biological pacemakers and to provide pacing therapy if the biological pacemaker is determined to be functioning improperly. Further, as noted previously, the pacemaker 200 may also include an ICD configured to provide cardioversion or defibrillation shocks if needed.

Figure 3:
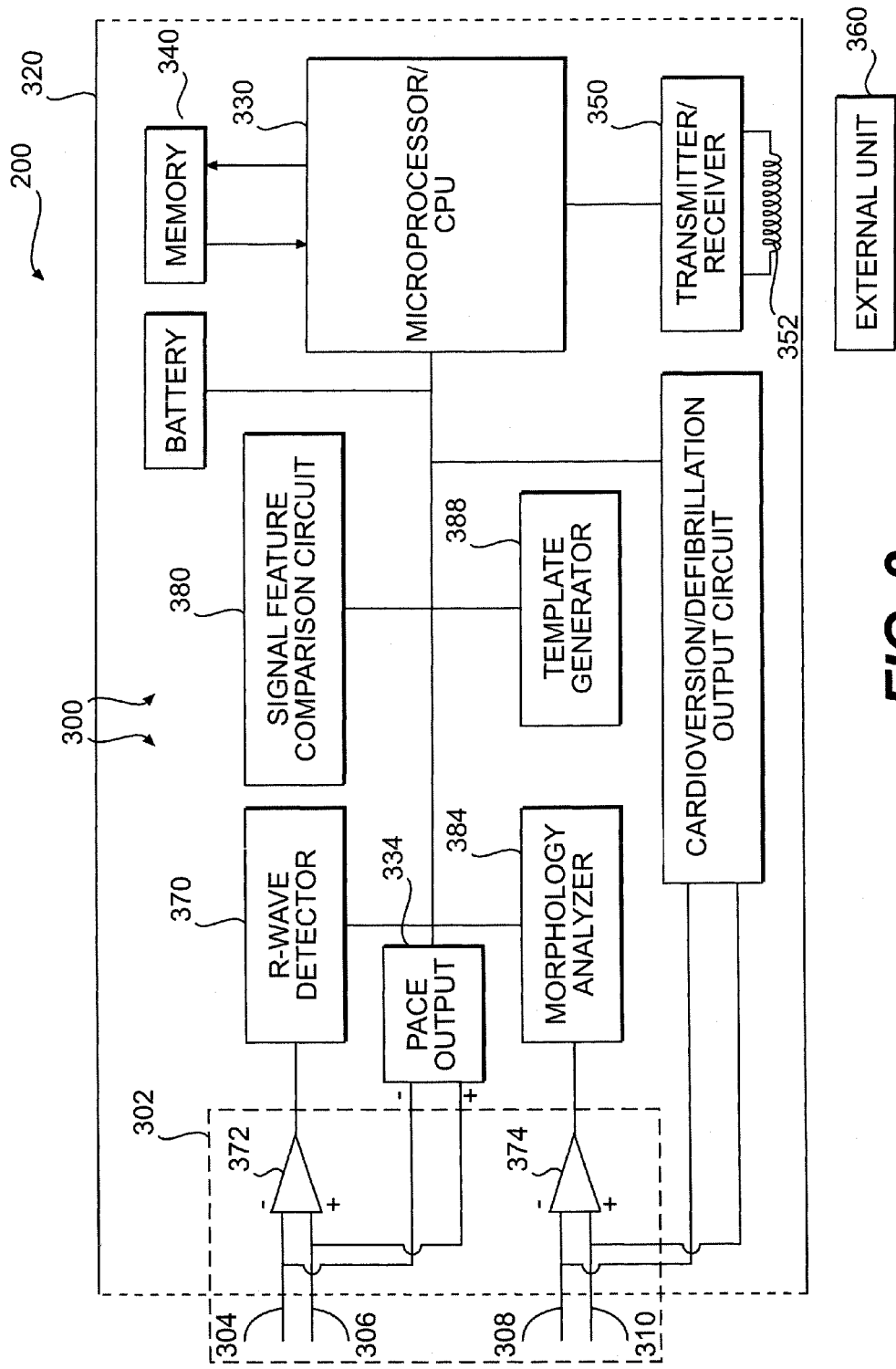
FIG. 3 illustrates a block diagram of the components of the pacemaker of FIG. 2.

Referring now to FIG. 3, there is shown a block diagram of one embodiment of pacemaker 200. The pacemaker 200 includes control system circuitry 300 for receiving cardiac signals from a heart and delivering electrical energy to the heart. The control system circuitry 300 includes a sensing system 302 attached to at least one catheter (e.g. leads). The sensing system 302 includes terminals 304, 306, 308, 310 for connection to electrodes attached to the surface of the leads. In one embodiment, the pacing leads 220, 222 are electrically connected to at least one of terminals 304, 306, 308, 310 and to the control system circuitry 300 through an electrically insulated conductor provided within the elongate body of the leads 220, 222.

In one embodiment, the control system circuitry 300 of the pacemaker 200 is encased and hermetically sealed in a housing 320 suitable for implanting in a human body as is known in the art. A connector block (not shown) is additionally attached to the housing 320 of the pacemaker 200 to allow for the physical and the electrical attachment of the leads 220, 222 to the pacemaker and the encased control system circuitry 300.

In one embodiment, the control system circuitry 300 of the pacemaker 200 is a programmable microprocessor-based system, with a microprocessor 330 and a memory circuit 340 which contains parameters for various pacing, defibrillation, and sensing modes, and stores data indicative of cardiac signals received by the control system circuitry 300. A transmitter/receiver circuit 350 is additionally coupled to the control system circuitry 300 and the memory circuit 340 to allow the pacemaker 200 to communicate with and receive programming instructions and transmit data to and from an external unit 360, as is known in the art. The transmitter circuit 350 may include any suitable wireless communication system. For example, the transmitter circuit 350 and the external unit 360 can use a wire loop antenna 352 and a radio frequency or inductive coupling telemetric link to receive and transmit signals and data to and from the external unit 360 and the control system circuitry 300. In this manner, programming commands or instructions are transferred to the microprocessor 330 of the pacemaker 200 after implantation, and stored cardiac data pertaining to sensed electrical activity or therapies applied to the heart are transferred to the external unit 360.

The pacemaker 200 may be configured to detect, measure, and/or record cardiac electrical signals. For example, leads 220, 222 may include one or more electrodes configured to facilitate near-field or far-field sensing, as is known in the art. Further, the sealed housing 320 of the pacemaker may serve as an electrode for stimulation and/or sensing. Additionally, other leads and electrodes may be positioned at suitable locations within the heart, or at other intracorporeal or extracorporeal locations.

The sensing electrodes may be electrically connected to a sense amplifier 372, 374, and the output of at least one sense amplifier 372 is connected to an R-wave detector 370. The R-wave detector 370 serves to sense and amplify cardiac signals, including cardiac complexes sensed from the heart, and to apply signals indicative thereof to a signal feature comparison circuit 380. The signal feature comparison circuit 380 is coupled to the microprocessor 330. Among other things, microprocessor 330 responds to signals from the R-wave detector 370 by providing pacing signals to a pace output circuit 334, according to the programmed pacing mode. In one embodiment, the pace output circuit 334 provides output pacing signals to terminals 304 and 306, which connect to the pacing electrodes of leads 220, 222.

In some embodiments, at least one pair of electrodes may be configured for far-field sensing. Further, sensed far-field signals may be connected with a second sense amplifier 374 that passes an amplified signal to a morphology analyzer circuit 384. The morphology analyzer circuit 384 receives and processes the cardiac complexes detected within the cardiac signals. In one embodiment, the morphology analyzer circuit 384 receives cardiac signals, including cardiac complexes representative of the cardiac cycle from the sensing system. Cardiac complexes analyzed by the morphology analyzer circuit 384 can include detected P-waves, QRS-complexes, and R-waves. In one embodiment, the morphology analyzer circuit 384 includes an analog filter for filtering cardiac signal noise sensed by the electrodes. In an exemplary embodiment, the cardiac signals are then band limited before arriving at an analog-to-digital filter which converts the analog signals into digital signals suitable for processing. In an alternative embodiment, the cardiac signals are filtered through an analog peak detector to extract the maximum and minimum cardiac signal values for each sensed cardiac complex.

In processing sensed cardiac complexes, the morphology analyzer circuit 384 windows a cardiac complex sensed in two or more cardiac signals. In one embodiment, the morphology analyzer circuit 384 locates and extracts information from one or more predetermined features of sensed cardiac complexes. The type of information extracted by the morphology analyzer circuit 384 can include the time of occurrence of one or more predetermined features and the amplitude values of the one or more predetermined features. In one embodiment, the predetermined features include regions of cardiac complexes that are repeatably identifiable in subsequent cardiac complexes. For example, such features may include a maximum deflection of the cardiac complex, a beginning of a cardiac complex as indicated by a predetermined deviation of the cardiac signal from a baseline signal, and an ending of a cardiac complex as indicated by a return of the first cardiac signal to a baseline signal. In one embodiment, the features are selectively programmed into the medical device system.

A template generator circuit 388 is coupled to the sensing system 302. The template generator circuit 388 receives information from the morphology analyzer 384. In one embodiment, the information received from the morphology analyzer 384 includes the information extracted from cardiac signals by the morphology analyzer circuit 384. In one embodiment, the template generator circuit 388 may create a numerical representation of sensed cardiac complexes using the extracted information. The template generator circuit 388 may then create an n-dimensional cardiac complex vector from these values as described below. In addition, the template generator circuit 388 may also create one or more classification vectors from a patient's own cardiac complexes as described below. Further, in other embodiments, the template generator circuit may evaluate time differences between fiducial points on two or more cardiac channels sensed during normal sinus rhythm. These time differences may be compared to time differences sensed in subsequent cardiac complexes to determine if the cardiac complexes originate in a biological pacemaker or another cardiac location.

Figure 4:
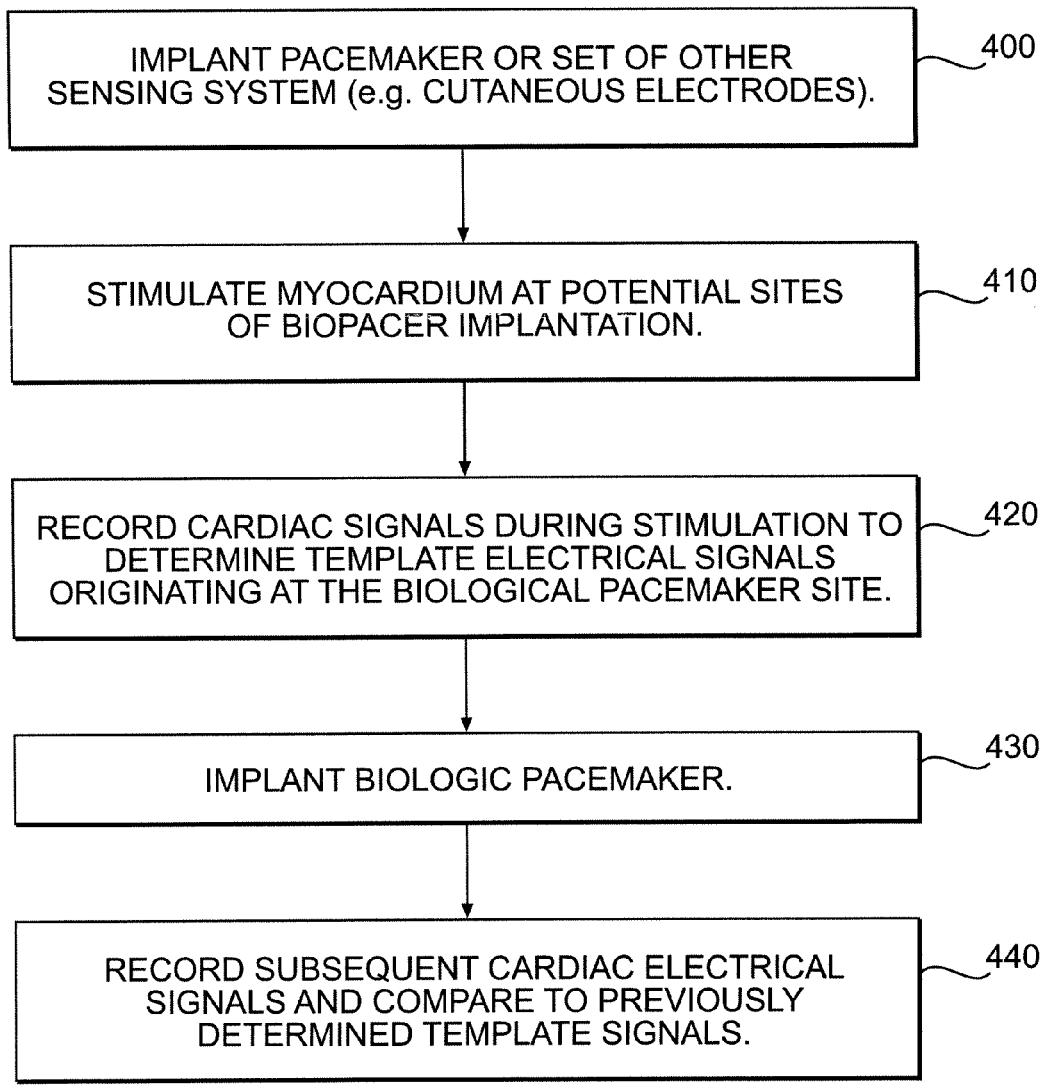
FIG. 4 illustrates a method for determining the origin of a sensed cardiac depolarization, according to an exemplary embodiment.

FIG. 4 illustrates a method for producing template electrical signals that may be used to evaluate the performance of a biological pacemaker and/or to determine if subsequent cardiac depolarizations originate within the biological pacemaker. As shown as shown at step 400, the process begins with implantation of the implantable pacemaker 200 or other implantable device, which may be used to measure and record cardiac electrical signals. It should be noted, as stated previously, the methods of the present disclosure may also be used with other types of sensing systems (e.g. external monitors or intravascular catheters, as used in electrophysiologic testing). However, use of an implantable pacemaker may be desirable when an implantable pacemaker is needed in combination with a biological pacemaker. Further, an implantable pacemaker may provide continuous and consistent monitoring and recording for ambulatory patients under real-life conditions. In addition, the implantable device may be configured strictly for monitoring and diagnosing with no pacing/stimulation capability.

Next, a physician may stimulate selected or potential sites for implantation of the biological pacemaker, as shown at 410. During stimulation, cardiac electrical signals may be recorded by the implanted pacemaker 200 or other sensing systems, and the sensed signals may be used to provide templates for comparison to subsequent signals, as shown at 420 and described in detail below.

Next, a physician may implant or inject the biological pacemaker into selected sites, as shown at 430. It should be noted that a physician may preselect a site for implantation of the biological pacemaker, or may determine the site of implantation by stimulating the myocardium and evaluating cardiac performance and/or electrical properties during stimulation. Further, as shown, determination of the template waveforms is performed before implantation of the biological pacemaker. However, in other embodiments, the biological pacemaker may be implanted first, and the template waveforms may be produced by stimulating the myocardium at or near of the site of implantation.

After implantation of the biological pacemaker, subsequent cardiac electrical signals may be sensed and compared to the template signals to evaluate the performance of the biological pacemaker and/or to determine if cardiac depolarizations originate in the biological pacemaker or in another cardiac location (e.g. SA node, implantable pacemaker electrodes, ectopic sites), as shown at 440. The subsequent cardiac signals may include sensed electrical signals from one or more channels. Further, the subsequent cardiac signals may include near-field and/or far-field signals.

In some embodiments, the methods of the present disclosure use two or more electrogram channels in a process of analyzing and classifying cardiac complexes. Each electrogram channel is used to sense a cardiac signal, wherein the cardiac signal includes cardiac complexes representative of at least a portion of a cardiac cycle. For example, portions of the cardiac cycle can include, but are not limited to, P-waves, QRS-cardiac complexes, and R-waves. Other portions of the cardiac cycle, including sensed signals of the entire cardiac complex, are considered useful and within the scope of the present disclosure.

In one embodiment, the present disclosure provides for two or more electrogram channels to simultaneously record cardiac complexes as they occur in the heart. As the cardiac complexes occur, each electrogram channel detects cardiac complexes representing portions of the cardiac cycle. The two or more electrogram channels are sensed at different cardiac locations, allowing for additional information about the same cardiac complex to be gathered during the same cardiac cycle. Each cardiac complex sensed with the two or more electrogram channels is placed in an analysis window where the cardiac complex is isolated. In one embodiment, each cardiac complex is windowed by isolating and plotting the portions of the simultaneously sensed cardiac complex in the two or more electrogram channels as they occurred in time.

Figure 5:
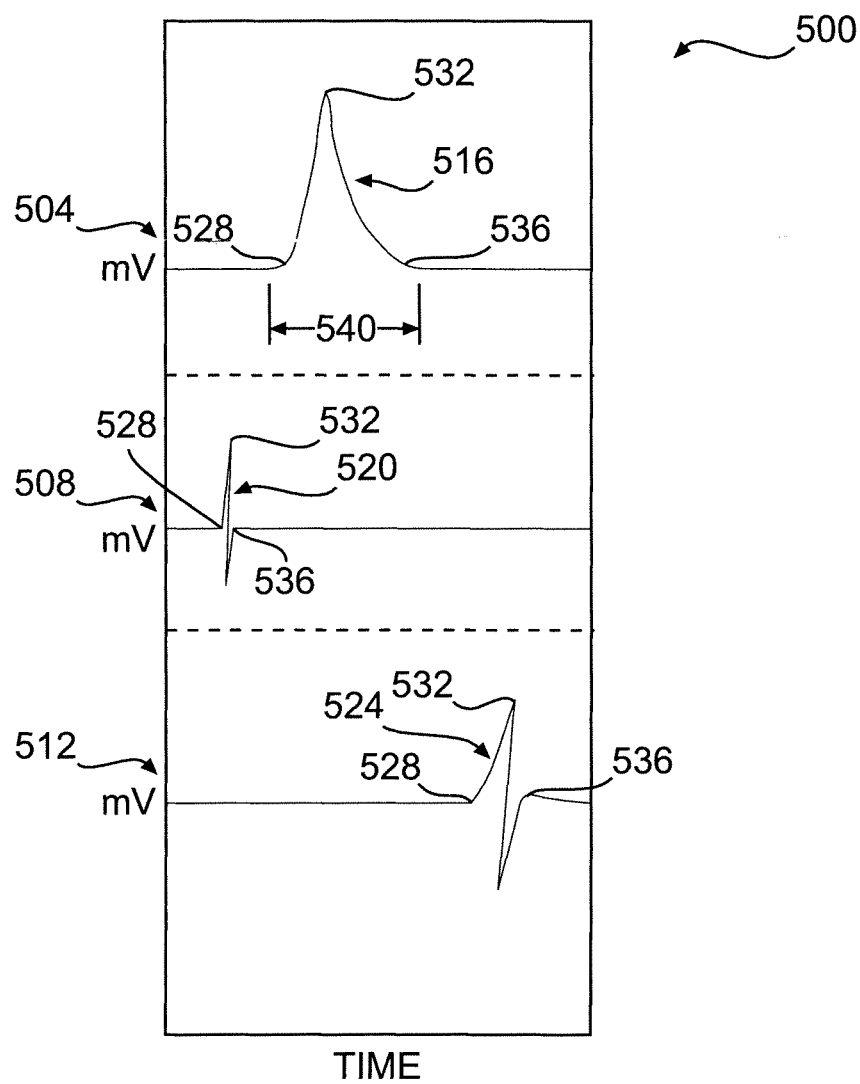
FIG. 5 illustrates one embodiment of a windowed cardiac complex sensed in three different cardiac locations, according to exemplary embodiments.

FIG. 5 illustrates one embodiment of a windowed cardiac complex 500 sensed in three different cardiac locations. In the present example, the windowed cardiac complex 500 has a first cardiac channel 504, a second cardiac channel 508, and a third cardiac channel 512. Cardiac complexes are sensed over the first cardiac channel 504, the second cardiac channel 508, and the third cardiac channel 512, wherein each cardiac channel may sense a different portion of the cardiac complex (e.g., R-wave, QRS-cardiac complex, P-wave). In the present example, the windowed cardiac complex 500 has three views of a cardiac complex as sensed over the three cardiac channels. A first cardiac complex 516 is shown in the cardiac signal sensed in the first cardiac channel 504. A second cardiac complex 520 is shown in the cardiac signal sensed in the second cardiac channel 508. Finally, a third cardiac complex 524 is shown in the cardiac signal sensed in the third cardiac channel 512. The first, second and third cardiac complexes 516, 520, 524 are representative of at least a portion of a single cardiac cycle. In one embodiment, the first, second and third cardiac complexes 516, 520, 524 are snapshots of the single cardiac cycle taken either at different locations within or on the heart and/or taken using different electrode configurations (e.g. far-field, near-field).

Cardiac information may be derived from the windowed cardiac complexes to produce a template for comparison to subsequent complexes. In one embodiment, information derived from the windowed cardiac complexes includes values derived or taken from one or more predetermined features on the cardiac complex sensed in each of the two or more cardiac channels. For example, predetermined features of the cardiac complexes that are useful in deriving information may include a maximum deflection of the cardiac complex, a beginning of a cardiac complex as indicated by a predetermined deviation of the cardiac signal from a baseline signal, an ending of a cardiac complex as indicated by a return of the first cardiac signal to a baseline signal, and a fiducial point (e.g. the point of greatest slope along the cardiac complex signal). In addition, other features of the cardiac complex signal may be useful for deriving information to produce template cardiac complexes. For example, one selection criteria for these additional features of a cardiac complex is that the feature is a repeatably identifiable portion of the cardiac complex. In general, amplitudes and slopes of cardiac complexes may be used as selection criteria. In addition, signals may be preprocessed by, for example, passing the signal through a differentiator. A derivative signal may be produced by the differentiator to select maximum or minimum points on a first derivative. These features may be used to provide consistent criteria for determining local activation time or tissue recovery from activation.

FIG. 5 shows several examples of predetermined features of the sensed cardiac complex that are useful in deriving information. In one embodiment, a beginning of the first, second and third cardiac complex 516, 520, 524 sensed in the first, second and third cardiac channel 504, 508, 512, respectively, is generally shown at 528. A maximum deflection point of the first, second and third cardiac complex 516, 520, 524 is shown generally at 532. Finally, an ending point of the first, second and third cardiac complex 516, 520, 524 is shown generally at 536.

In one embodiment, the cardiac complexes sensed in the two or more cardiac channels are windowed with each of the signals of the cardiac complexes represented as a voltage as a function of time. FIG. 5 shows an example of the first, second and third cardiac complex (516, 520 and 524) sensed in the first, second and third cardiac channel (504, 508 and 512) being plotted as voltage as a function of time. Once the cardiac complex sensed in the two or more cardiac channels is represented in this fashion, information can be derived from the specific features of the cardiac complexes.

In one embodiment, the information derived from the cardiac complexes in each of the cardiac channels is the time a repeatably identifiable feature of the cardiac complex occurred. Alternatively, the information derived is a time difference between pairs of repeatably identifiable features on a cardiac complex sensed in one of the two or more electrogram channels. In one embodiment, a first time difference 540 is between the beginning 528 of the first cardiac complex 516 and the end 536 of the first cardiac complex. In an additional embodiment, the information derived is a time difference between pairs of repeatably identifiable features on two different cardiac complexes sensed in two electrogram channels. In a further embodiment, the information derived is a combination of the time difference between pairs of repeatably identifiable features on two different cardiac complexes sensed in two electrogram channels and the time differences from pairs of repeatably identifiable features on a cardiac complex sensed in one of the two or more electrogram channels.

Information from multiple cardiac channels can be used to represent the cardiac complex to generate a template cardiac complex and to compare subsequently-sensed complexes to the template. In one embodiment, the cardiac complex sensed in multiple cardiac channels can be numerically represented. One way of numerically representing the cardiac complex is to use scalar values derived from the cardiac signals of the cardiac complex. Further, in one embodiment, the scalar values derived from the cardiac signals of the cardiac complex are the times repeatably identifiable features of the cardiac complex occur. Alternatively, time differences between the repeatably identifiable features, as previously described, are used to derive the scalar values. In an additional embodiment, the scalar values can be derived from a magnitude of the position of the predetermined feature for each of the two or more cardiac signals. In one embodiment, the magnitude of the position of the predetermined feature is the voltage measurement of the maximum deflection position along the cardiac signal.

The values derived for a cardiac complex are then used to create an n-dimensional cardiac complex vector. In one embodiment, the cardiac complex vector has the form: A=[A1, A2, A3, . . . An], where each of the values, A1-An, represent scalar values derived from the repeatably identifiable features of the cardiac complex. The cardiac complex vector (A) represents the cardiac complex and is used to identify and classify the cardiac complex. In one embodiment, cardiac complexes sensed during stimulation at a site selected for implantation of a biological pacemaker, as indicated at Steps 410-430 of FIG. 4, are used to produce template cardiac complex vectors that may be compared to vectors derived from subsequently-sensed cardiac complexes, as indicated at Step 440. In other embodiments, the template vector may be a predefined classification vector derived from cardiac complexes sensed over two or more cardiac channels for a population of patients. In some embodiments, the template vector may be created using stimulation and recording techniques, as used for cardiac pacemapping. Pacemapping is described in Moreno et al, "Pacemapping: Review Article," Indian Pacing and Electrophysiology Journal Vol. 5(1): 35-42 (2005)

In one embodiment, the template vectors may have the form: C=[C1, C2, C3, . . . Cn], where each of the values C1-Cn represent scalar values derived from the repeatably identifiable features of the cardiac complexes. In one embodiment, each of the values C1-Cn are average values derived from repeatably identifiable features of the cardiac complexes for the patient population. In an alternative embodiment, each of the values C1-Cn are median values derived from repeatably identifiable features of the cardiac complexes for the patient population. One or more of the predetermined template vectors can then be used in the implantable medical device to determine the origin of subsequently-sensed cardiac complexes.

Figure 6:
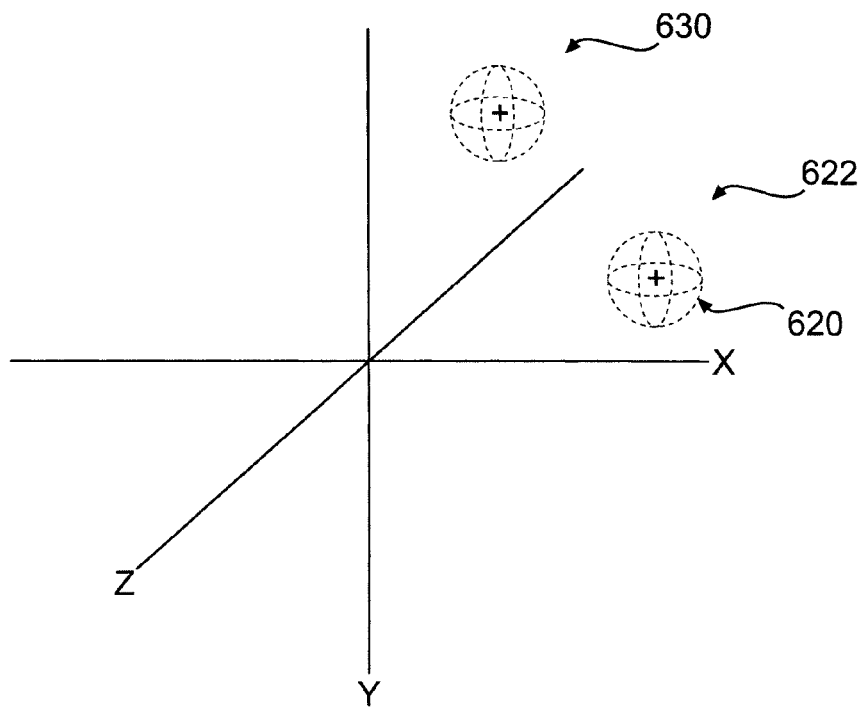
FIG. 6 illustrates a template cardiac complex vector and a subsequently-sensed cardiac complex vector, according to an exemplary embodiment.

In one embodiment, determining whether a cardiac complex should be grouped with one or more classified cardiac complexes is accomplished through a process of comparing the complex vector (A) of the cardiac complex to be classified with the complex vector (A) of the cardiac complex representing template cardiac complexes. FIG. 6 shows an embodiment of a template cardiac complex vector 622 and a subsequently-sensed and determined cardiac vector 630. As shown, the cardiac complex vectors 622, 630 are plotted in a Cartesian coordinate system with three-dimensions. Cardiac vectors plotted in FIG. 6 have three values A=[A1, A2, A3]. As noted previously, the template vector 622 may be determined by stimulating a cardiac region selected for implantation of a biological pacemaker, or by deriving information related to a population of patients having a similarly-placed biological pacemaker.

The cardiac vector 622 of the template cardiac complex may be used to determine whether subsequently-sensed cardiac complexes originate in an implanted biological pacemaker or in another cardiac location. In one embodiment, to determine whether subsequently-sensed cardiac complexes originate in the biological pacemaker the subsequently-sensed cardiac complex vector 630 may be compared to the cardiac vector 622 of the template cardiac complex. In some embodiments, a first region 620 representing a volume in the Cartesian system of FIG. 6 may be selected. If the cardiac vector 630 representing the subsequent cardiac complex falls on or within the first region 620, the subsequent cardiac complex is classified as a complex originating in the biological pacemaker. In an alternative embodiment, if the cardiac vector representing the subsequent cardiac complex falls outside the first region 622, the subsequent cardiac complex may be used to create a second class of cardiac complexes.

In addition, cardiac vectors may be derived for cardiac complexes originating in other cardiac locations. For example, cardiac vectors representing complexes originating at the sites of one or more pacing leads may be determined. In addition, cardiac vectors representing complexes originating in a native SA node or an ectopic cardiac focus may be determined. In some embodiments, a physician may stimulate a heart at various regions near a selected site (e.g. a node, a pacemaker electrode site, a known ectopic focus, etc.), and cardiac complexes may be monitored during resulting cardiac depolarizations. These complexes may be recorded and used as templates to classify subsequent cardiac complexes. Further, vectors derived form subsequently-sensed cardiac complexes may be compared to vectors representing complexes originating in other cardiac locations to determine the origin of subsequent cardiac complexes.

Figure 7:
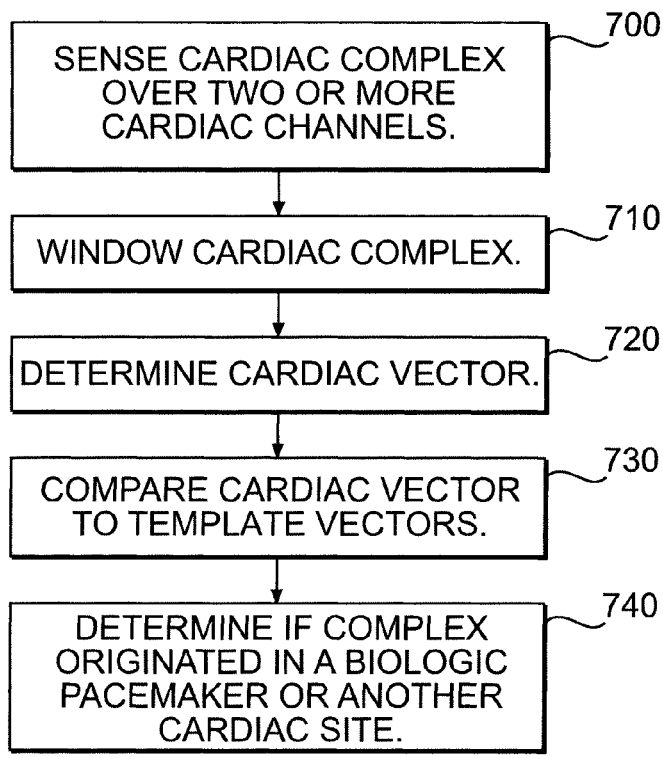
FIG. 7 illustrates a method for determining the origin of a sensed cardiac depolarization, according to another exemplary embodiment.

FIG. 7 shows one embodiment of a method of the present disclosure. At 700, two or more cardiac signals representative of electrical cardiac activity are monitored. The cardiac signals are monitored to detect cardiac complexes occurring in two or more cardiac signals. In one embodiment, an implantable medical device is used to detect cardiac complexes in the two or more cardiac signals. Further, the implantable medical device may include two or more cardiac electrodes that allow for near-field and/or far-field cardiac signals to be sensed from a heart.

At 710, the cardiac complex present in the two or more cardiac signals is isolated in an analysis window (or "windowed" for analysis). As previously discussed, windowing isolates a section, or portion, of the two or more cardiac signals, each containing a view of the cardiac complex that is being evaluated. After the cardiac signals containing the cardiac complex have been isolated, at least one predetermined feature is located in the cardiac complex present in each of the two or more cardiac signals.

Once the cardiac signals containing the cardiac complex have been windowed, scalar values from predetermined features of the cardiac complex are generated. In one embodiment, the scalar values are generated as a function of the position of the predetermined feature, or features, on each of the two or more cardiac signals. The scalar values are then used to create a cardiac vector, where the cardiac vector represents the cardiac complex.

Figure 8:
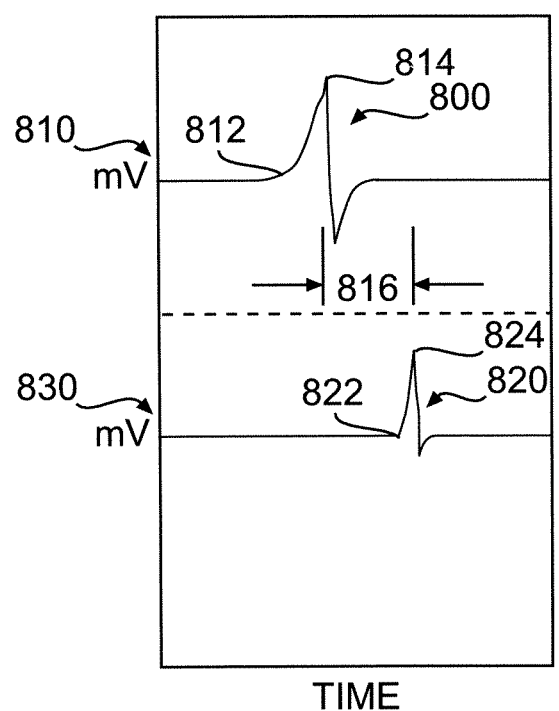
FIG. 8 illustrates one embodiment of cardiac complexes of a cardiac cycle windowed for analysis and classification.

FIG. 8 shows one embodiment of cardiac complexes of a cardiac cycle windowed for analysis and classification. A first cardiac complex 800 is present in a first cardiac signal 810 and a second cardiac complex 820 is present in a second cardiac signal 830. As previously discussed, the two or more cardiac signals are sensed simultaneously from the heart, and so the first cardiac complex 800 and the second cardiac complex 820 are representative of portions of a complete cardiac cycle occurring in the heart.

Predetermined features of the cardiac complex in each cardiac signal are used to derive a cardiac vector. In the present example, the cardiac vector is programmed to have four values, such that A=[A1, A2, A3, A4]. Each of the values A1-A4 represent scalar values derived from the repeatably identifiable features of the cardiac complex. In one embodiment, A1 is programmed to be the beginning time 812 of the first cardiac complex 810, A2 is programmed to be the time of the maximum deflection point 814 of the first cardiac complex 810, A3 is programmed to be the time difference 816 between the time of the maximum deflection point 814 and the time of the maximum deflection point 824 of the second cardiac complex 820, and A4 is programmed to be the beginning time 822 of the second cardiac complex 820.

Referring again to FIG. 7, after a cardiac vector has been determined for the cardiac complex (as shown at 720), the cardiac vector is compared to one or more template vectors at 730. In one embodiment, the cardiac vector is compared to the template vectors to determine whether the cardiac vector is similar enough to one or more template vectors to determine the origin of cardiac complex. Further, a similarity coefficient may be determined from each comparison of the cardiac vector and the one or more template vectors. Based on this similarity coefficient, the cardiac complex is classified as a complex originating in an implanted biological pacemaker or another cardiac location (e.g. a pacemaker electrode site, an SA node, or an ectopic site). In one embodiment, a mean square error is used to determine the similarity coefficient. The mean square error value may be represented as $\Sigma(A_i-C_i)^2 \leq X$, where $A_i$ represents the ith scalar value (A1-An) of the cardiac vector, $C_i$ represents the ith scalar value (C1-Cn) of the classification vector and X is a predetermined threshold value. In one embodiment, the predetermined threshold value X defines the region or a neighborhood around the template vector which is deemed to be sufficiently close to permit classifying the cardiac complex represented by the cardiac vector as originating at the site of the template vector, as shown at 740.

In an additional embodiment, prior to comparing the sensed cardiac vector to the template vectors, the cardiac vector is aligned, or coordinated with, each of the template vectors. In one embodiment, the cardiac vector and the classification vectors include element positions (A1 and C1 are in the first element position, A2 and C2 are in the second element position, etc.) which are occupied by the scalar values. The cardiac vector and a template vector are aligned around the scalar values in the same element position (i.e., a coordinating element position) in both the cardiac vector and the classification vector.

In one embodiment, the process of aligning the cardiac vector and the template vector involves adjusting each scalar value of the cardiac vector so one of the element positions of the cardiac vector equals a scalar value in a corresponding element position in a template vector. When the scalar values in the vectors are the time of occurrence of features in different channels, the vectors are aligned by adding or subtracting an appropriate numerical value to all the elements of the cardiac vector (e.g., the scalar values in the cardiac vector) so that the scalar value in the coordinating element position of the cardiac vector has the same numerical value as the coordinating element position of the classification vector.

In one embodiment of aligning a cardiac vector and a template vector, a cardiac complex is sensed two or more cardiac channels, from which a cardiac vector A=[A1, A2, A3, A4] is determined. In this embodiment, the elements of the vector are times at which the repeatably identifiable features of the cardiac complex occurred in the two or more cardiac channels. One or more template vectors are provided having the general form C=[C1, C2, C3, C4]. In one embodiment, the cardiac vector is aligned, or coordinated, around the same element position (the coordinating element) with the template vector to which the cardiac complexes are compared. In one embodiment, the coordinating element is the first position in the cardiac vector and the template vector, A1 and C1. A numerical value Y is added to, or subtracted from, the value of A1 so that A1 equals C1. So, A1+Y=C1, where Y can have either a positive or a negative numerical value. In addition to modifying the value of A1 with Y, Y is also added to the remaining elements of the cardiac vector. So, a cardiac vector aligned with a template vector has the form A=[A1+Y, A2+Y, A3+Y, A4+Y], where A1+Y=C1 of the template vector C=[C1, C2, C3, C4]. After the cardiac vector has been aligned with the template vector, the elements of the vectors, excluding the coordinating elements, are compared. This means that for the present example, the vector A=[A2+Y, A3+Y, A4+Y] would be compared to the template vector C=[C2, C3, C4]. Finally, the cardiac vector can be aligned with a template vector around any element (e.g., A1/C1, A2/C2, etc.) in the pair of vectors.

As previously discussed, the methods of the present disclosure may include using two or more electrogram channels in a process of analyzing and classifying cardiac complexes. In one embodiment, a first cardiac signal and a second cardiac signal are sensed over a first electrogram channel and a second electrogram channel, respectively. During a template generation period, a cardiac complex is detected in the first cardiac signal and the second cardiac signal. The morphology of the first cardiac signal and the second cardiac signal representing the template cardiac complex can then be compared to subsequently-detected cardiac complexes. Based on this comparison, the origin of the subsequently-sensed cardiac complexes can be determined. Further, in some embodiments, the origin of the subsequently-sensed cardiac complexes will be evaluated to determine if the cardiac complex originates at the site of an implanted biological pacemaker, or at another cardiac location.

In some embodiments of the present disclosure, two or more cardiac signals may be evaluated to determine if a cardiac complex originates in a ventricular biological pacemaker, or in a supraventricular cardiac location. As noted previously, in some embodiments of the present disclosure, time differences between repeatably identifiable points sensed in two or more simultaneously-recorded cardiac channels may be determined. Further, similarly recorded cardiac signals for subsequently-sensed cardiac complexes may be evaluated to determine time differences between corresponding repeatably identifiable points in the subsequent cardiac complexes. As described in detail below, the time difference for the first and subsequent cardiac complexes may be compared to determine if the subsequent cardiac complex originated in a ventricular biologic pacemaker, or another pacemaker location. U.S. Pat. No. 6,959,212, issued to Hsu et al. on Oct. 25, 2005, describes methods for differentiating between supraventricular and ventricular tachycardias. The methods of Hsu et al. for determining repeatably-identifyable points may be used whenever possible. The repeatably-identifiable points and intervals used to differentiate between supraventricular and ventricular tachycardias may also be used to identify cardiac complexes originating in a ventricular biological pacemaker. This patent is herein incorporated by reference in its entirety.

In one embodiment, while stimulating the heart, a first cardiac signal and a second cardiac signal are sensed over a first electrogram channel and a second electrogram channel, respectively. In some embodiments, the first channel may correspond to a near-field cardiac channel, and the second channel may correspond to a far-field channel. As the cardiac complexes are sensed, predetermined features are located along each of the near-field and far-field signals for the cardiac complexes. In one embodiment, a template time difference is calculated from timing differences for a plurality of cardiac electrical activation sequences (e.g., QRS-cardiac complexes) sensed in subsequent cardiac complexes. In one embodiment, the template time difference is the median time difference between the relative timing of features on the cardiac signal sensed in each of a plurality of sensing channels during a NSR. In an alternative embodiment, the template time difference is the average time difference between the relative timing of features on the cardiac signal sensed in each of a plurality of sensing channels during NSR. Therefore, in one embodiment, a timing difference is determined between the predetermined feature, or features, on the near-field signal and the predetermined feature, or features, on the far-field signal for each sensed cardiac complex.

In other embodiments, the template time difference is the median time difference between the relative timing of features on the cardiac signal sensed in each of a plurality of sensing channels during a cardiac depolarization originating in any supraventricular location. For example, any cardiac depolarization originating in the SA node may be selected, even if the patient is known to have a sinus arrhythmia. Further, in some embodiments, the template time difference may be determined while stimulating the heart using an atrial cardiac lead, such as lead 222 of FIG. 2, or any other atrial lead.

Figure 9:
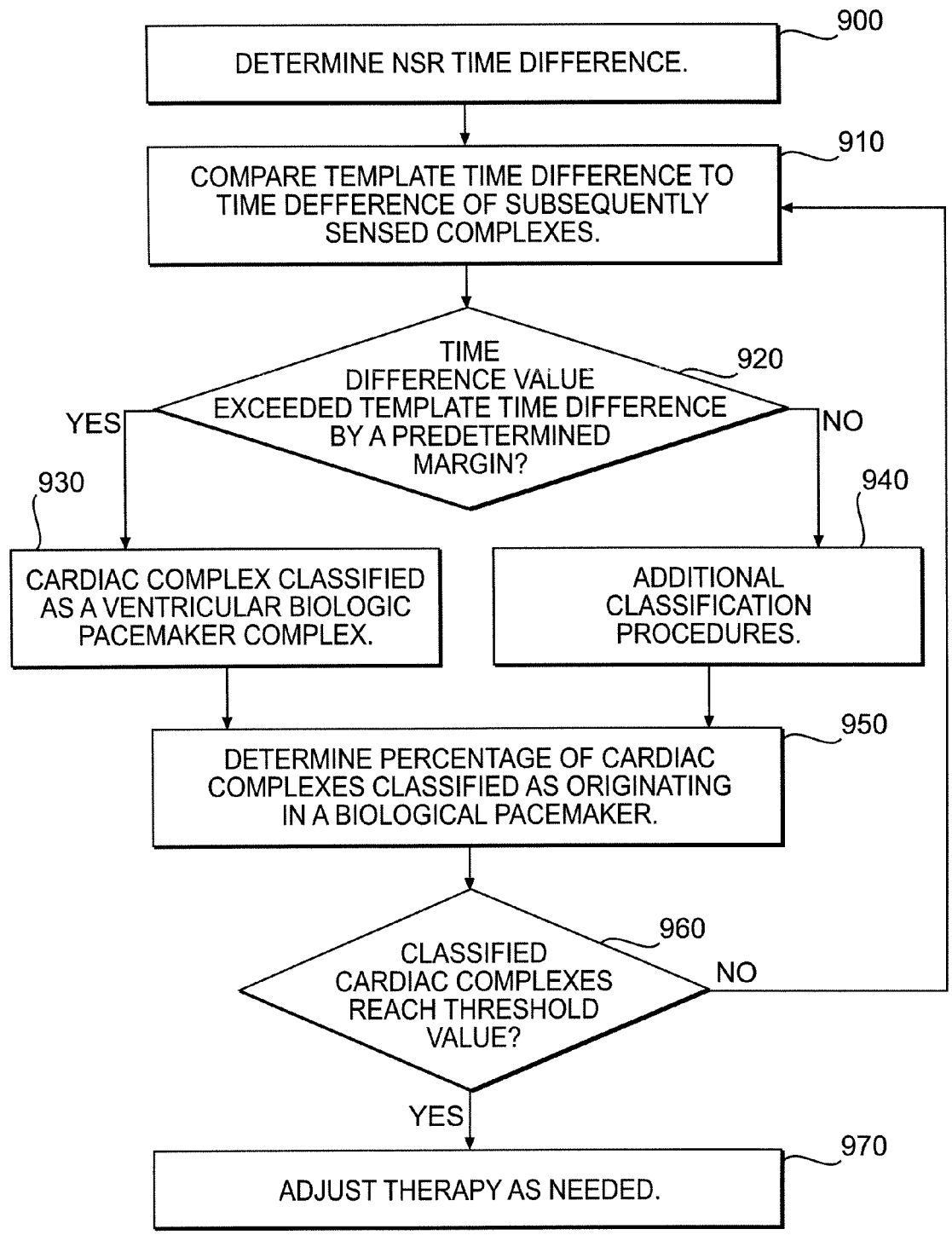
FIG. 9 illustrates a method for comparing time differences to determine if a cardiac depolarization originates in a ventricular biological pacemaker or another cardiac location, according to an exemplary embodiment.

FIG. 9 illustrates a method for comparing time differences to determine if a cardiac depolarization originates in a ventricular biological pacemaker or another cardiac location. First, a template time difference is calculated for repeatably identifiable features of cardiac complexes sensed in two or more cardiac locations during NSR, as shown at 900. Next, as shown at 910, the template time difference is compared to time differences determined from at least one subsequently-sensed cardiac complex. In one embodiment, the time difference of the subsequently-sensed complex is calculated using the same method used to acquire and compute the time differences during NSR (i.e. with the same lead configuration and using the same repeatably identifiable points on the complex). Based on the comparison, a decision is made at 920 whether the time difference value exceeds the template time difference value by a predetermined margin. Next, when the time difference exceeds the template time difference by the predetermined margin, the cardiac complex is classified as a ventricular biological pacemaker complex, as shown at 930. However, if the time difference does not exceed the template time difference by the predetermined margin, the system proceeds to 940. As noted previously, the time difference determined at Step 900 may be a NSR time difference. However, any suitable supraventricular rhythm may be selected for determining a template time difference.

At 940, the system may utilize additional procedures to classify the cardiac complex as either a biological pacemaker complex or non-biological pacemaker. For example, in some embodiments, cardiac vectors representing the ventricular biological pacemaker complex may be compared to subsequently-sensed cardiac complexes, as described previously. In addition, morphology comparison algorithms may be used to determine a degree of correlation between cardiac complexes originating in the site of a biologic pacemaker and subsequently-sensed cardiac complexes. If the additional classification procedures determine the cardiac complex to be a non-biological pacemaker complex the system passes the information to 950 and then returns to 900 to continue to sense and analyze cardiac complexes. Alternatively, if the additional classification procedure classifies the cardiac complex as a ventricular biological pacemaker complex the information is passed to 950 where the percentage of cardiac complexes classified as having a biological pacemaker origin.

As noted, values derived from characteristics of sensed cardiac complexes are compared to values derived from cardiac complex characteristics sensed during NSR, or from otherwise suitable supraventricular complexes. In one embodiment, the values compared are timing differences between morphological characteristics or characteristic values on at least two different cardiac sensing channels (e.g., far-field signals and near-field signals) for cardiac complexes sensed during NSR or other suitable rhythm and for subsequently-sensed cardiac complexes.

In one embodiment, the values for timing differences between the morphological characteristics from the different cardiac sensing channels are calculated, stored and subsequently used by comparing them to the timing differences calculated from the corresponding morphological characteristics or characteristic values of subsequently-sensed cardiac complexes. Based on the comparison between the NSR characteristic value (e.g., the timing differences between the morphological characteristics) and the characteristic value for the subsequently-sensed cardiac complexes, the subsequently-sensed cardiac complex is classified as either being a biological pacemaker complex or a complex originating in another location. Finally, it is possible to use a combination of timing differences between the morphological features on cardiac complex signals and morphological characteristics of cardiac complexes sensed using at least two different types of cardiac sensing channels, such as far-field and near-field sensing.

For example, the two or more simultaneous sensing channels may include both a far-field channel and a near-field channel. In providing two or more simultaneous sensing channels, cardiac complexes of the heart are being sensed from at least two different cardiac locations, so sensed cardiac complexes may include at least a first signal representative of electrical activity of the heart sensed at a first cardiac region, and a second signal representative of electrical activity of the heart is sensed at a second cardiac region. In the present embodiment, the sensed cardiac signals include cardiac electrical activation sequences (e.g., QRS-cardiac complexes) representative of a cardiac cycle.

In one embodiment, the first cardiac region and the second cardiac region are in or adjacent ventricular regions of the heart. This allows for ventricular activity to be sensed in a plurality of locations by the medical device system. In an alternative embodiment, both an atrial region of the heart and a ventricular region of the heart are used as the first cardiac region and the second cardiac region. For example, one of the first cardiac region or the second cardiac region is a ventricular region of the heart, such as the right ventricle, while the remaining cardiac region is an area of the patient's heart sensed across, or in, both the ventricular and atrial regions of the heart.

As noted previously, the medical device system can also be configured to sense any combination of cardiac near-field signals (rate signals) and/or far-field signals (morphology signals). This will depend upon the electrode system employed to sense each cardiac region in the heart. In one embodiment, two or more cardiac near-field signals are sensed from two or more cardiac regions in the heart. In an alternative embodiment, two or more cardiac far-field signals are sensed from two or more cardiac regions in the heart. In an additional embodiment, at least one of a cardiac far-field signal and at least one of a cardiac near-field signal are sensed from two or more cardiac regions in the heart. Additionally, cardiac signals can be sensed by electrodes positioned on the housing of an implantable system.

As noted, in one embodiment, a template may be derived from timing differences between features on the cardiac signals. In deriving the timing difference, the medical device system first determines the occurrence of a first feature on the first cardiac signal and a second feature on the second cardiac signal. In one embodiment, the morphology analyzer circuit 384 is used to locate features along the cardiac signals received by the pacemaker 200, and the first feature and the second feature are based on a selection criteria, such as repeatably identifiable regions in subsequent cardiac complexes. In another embodiment, the selection criteria may include a point at the beginning of the sensed cardiac signal that is determined by sensing a predetermined deviation of the first signal from a baseline signal of the first signal and of the second signal from a baseline signal of the second signal.

Alternatively, other selection criteria may be used to determine what repeatably identifiable features are used. For example, the selection criterion may include a maximum deflection point of the cardiac signal, such as a maximum absolute value (i.e., largest maximum or minimum value) point along either the first cardiac signal or the second cardiac signal. In an additional embodiment, the selection criterion is a point at the end of the sensed cardiac signal, which may correspond to the point at which a QRS-cardiac complex returns to a baseline value. The selection criterion can also be the fiducial point along the sensed cardiac signal, where the fiducial point is the point along the cardiac signal with the largest first derivative of the electrogram signal (i.e., the point of largest slope along the sensed QRS-cardiac complex signal). The selection criterion is any repeatably identifiable feature along sensed cardiac signals.

Figure 10:
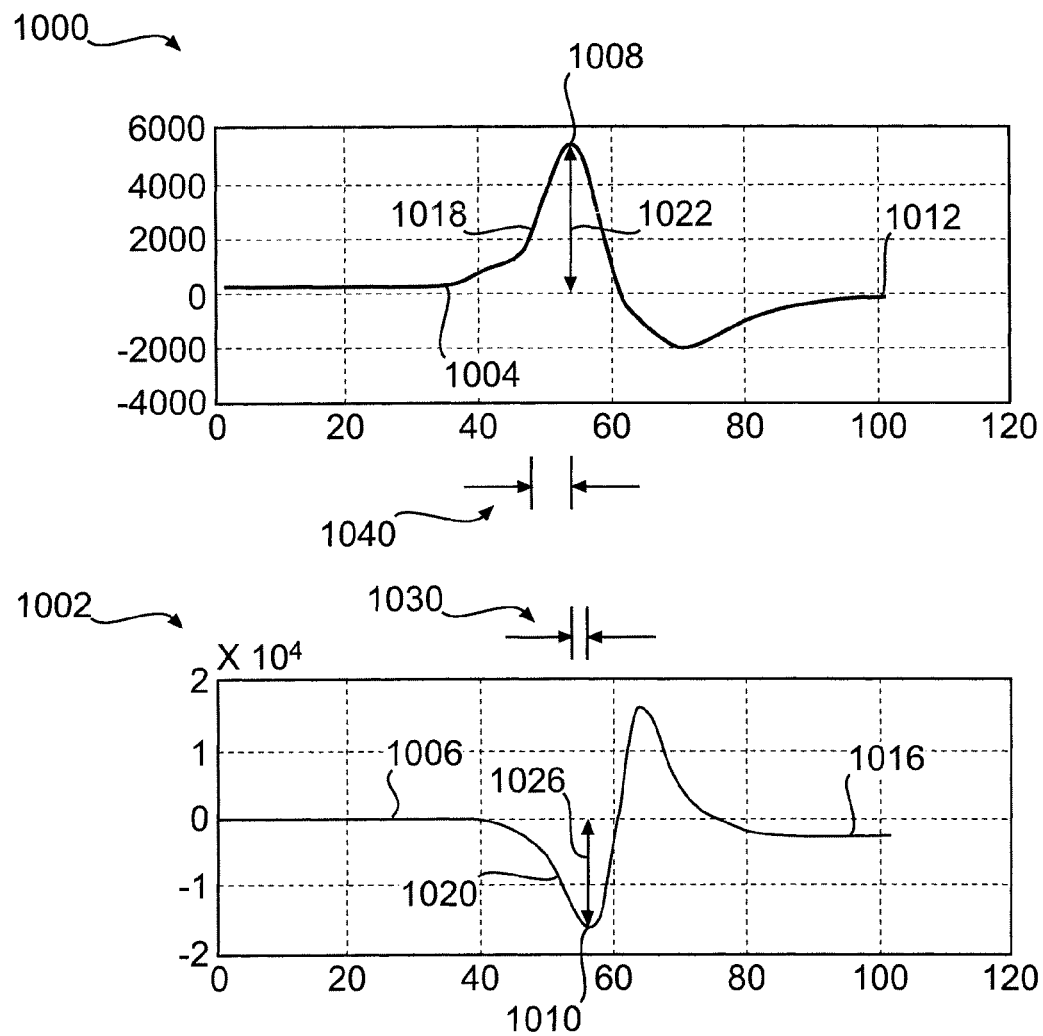
FIG. 10 illustrates cardiac complexes sensed with near-field and far-field sensing systems, according to an exemplary embodiment.

FIG. 10 illustrates cardiac complexes sensed with near-field and far-field sensing systems, according to an exemplary embodiment. As shown, FIG. 10 illustrates examples of the possible selection criteria useful with the present system. FIG. 10 shows examples of a first cardiac signal 1000 and a second cardiac signal 1002 of a cardiac electrical activation sequence (e.g., a QRS-cardiac complex). In the present embodiment, the first cardiac signal 1000 and the second cardiac signal 1002 were recorded during normal sinus rhythm. The first cardiac signal 1000 is an example of a far-field cardiac signal, and the second cardiac signal 1002 is an example of a near-field cardiac signal. As previously mentioned, a variety of selection criterion can be selected and use to identify features along the cardiac signals that are repeatably identifiable. For example, in one embodiment, the selection criterion includes a point at the beginning of the QRS-cardiac complex. In one embodiment, this point is shown approximately at 1004 for the first cardiac signal 1000 and at 1006 for the second cardiac signal 1002.

In an alternative embodiment, the selection criterion is a maximum absolute value (i.e., largest maximum or minimum value) point of the QRS-cardiac complex. FIG. 10 shows the maximum deflection point (largest absolute peak) of the cardiac signal at approximately 1008 for the first cardiac signal 1000 and 1010 for the second cardiac signal 1004. In one embodiment, the maximum point of the QRS-cardiac complex is indicated by a point in the first signal and the second signal having approximately the largest deflection from a baseline signal. In one embodiment, the baseline signal is the approximate value of the signal between the occurrence of QRS-cardiac complexes. The location and size of the maximum point of the QRS-cardiac complex will depend upon the location and type electrodes used to sense the heart.

In an additional embodiment, the selection criterion is a point at the end of the cardiac electrical activation sequence (the QRS-cardiac complex), which may be denoted by the first signal and the second signal returning to a baseline value after the occurrence of an intrinsic contraction of the heart. FIG. 10 shows the point at the end of the sensed cardiac signal approximately at 1012 for the first cardiac signal 1000 and at 1016 for the second cardiac signal 1004. In a further embodiment, the selection criterion is a fiducial point, which is shown at approximately 1020 on the second cardiac signal 1004.

In an alternative embodiment, characteristics of the cardiac signal are used to create the template. For example, the slope of the cardiac signal may be used as the selection criteria, where the slope is taken along the first major inflection of the cardiac signal as shown at approximately at 1018 for the first cardiac signal 1000 and at 1020 for the second cardiac signal 1004. In an additional embodiment, the amplitude of the amplitude of the maximum deflection point is used to create the template. One embodiment of the amplitude of a maximum deflection point is shown at 1022 for the first cardiac signal 1000 and at 1026 for the second cardiac signal 1004. In an alternative embodiment, the characteristic used to determine the template is the slew rate of the cardiac signals sensed during normal sinus rhythm.

Referring again to FIG. 9, at step 910 the time difference between features on the cardiac complexes are determined for the cardiac complexes sensed during normal sinus rhythm. Because the cardiac complexes are being sensed at different cardiac locations (e.g., the first cardiac location and the second cardiac location), there is an inherent difference in the time that the cardiac complexes will be sensed. As a result, the timing difference can be taken between corresponding features on cardiac complexes. For example, in FIG. 10 there is a time difference 1030 between 1008 and 1010 when the selection criterion is a maximum deflection point of the cardiac complex. In an additional example, there is a time difference 1040 between the largest absolute peak 1008 in the first cardiac signal 1000 and the fiducial point 1020 in the second cardiac signal 1004.

In addition to determining time differences between corresponding features on cardiac complexes, it is also possible to determine timing differences between different combinations of features on the cardiac complexes. When more than two cardiac complexes are sensed, time differences between the selected features for any or all of the combinations of cardiac complexes may be used to create the template for the normal sinus rhythm complex.

In some embodiments, a morphological comparison may be made between template complexes sensed in first and second cardiac channels and subsequently-sensed complexes. For example, when the medical device system senses subsequent cardiac complexes, a signal amplitude of the first feature point and the second feature point for a sensed cardiac complex is determined. In one embodiment, the signal amplitude for the first feature and the second feature are calculated relative to the baseline signal of the first signal and the second signal respectively. The signal amplitude of the first feature point and the second feature point are then compared to the corresponding median signal amplitude of the first feature point and the second feature point, and if the signal amplitude of at least one of the first feature and the second feature exceeds the corresponding median signal amplitude of the first feature and the second feature by a predetermined amount, the cardiac complex is characterized as a biological pacemaker complex.

Other features of the first signal and the second signal are also useful in determining whether a cardiac complex is a biological pacemaker complex. In one embodiment, the medical device system senses the first signal representative of electrical activity at a first cardiac region, where the first signal includes a QRS-complex representative of a cardiac cycle. The medical device system also senses the second signal representative of electrical activity at a second cardiac region, where the second signal including the QRS-complex as sensed in the second cardiac region. Initially, a representative slope value for both the first signal and the second signal is determined from a plurality of normal sinus rhythm complexes. In one embodiment, the representative slope value is a median slope value derived from the plurality of normal sinus rhythm complexes.

Subsequently, the medical device system senses cardiac complexes (e.g., QRS-cardiac complexes) and determines a first slope for the first signal and a second slope for the second signal. In one embodiment, both the first signal and the second signal are maximum slopes (the fiducial point) for both the first signal and the second signal. The medical device system then compares the maximum slope of the first signal and the second signal of the QRS-cardiac complex to the corresponding representative slope for the first signal and the second signal. Based on this comparison, if the slope of at least one of the first signal and/or the second signal deviates from the corresponding representative slope for the first signal and the second signal by a predetermined amount, the cardiac complex is characterized as a biological pacemaker complex. In one embodiment, the predetermined amount is based on the percent deviation of the first signal and/or the second signal from the corresponding representative slope, where the predetermined amount is greater than or equal to 20% deviation.

Figure 11:
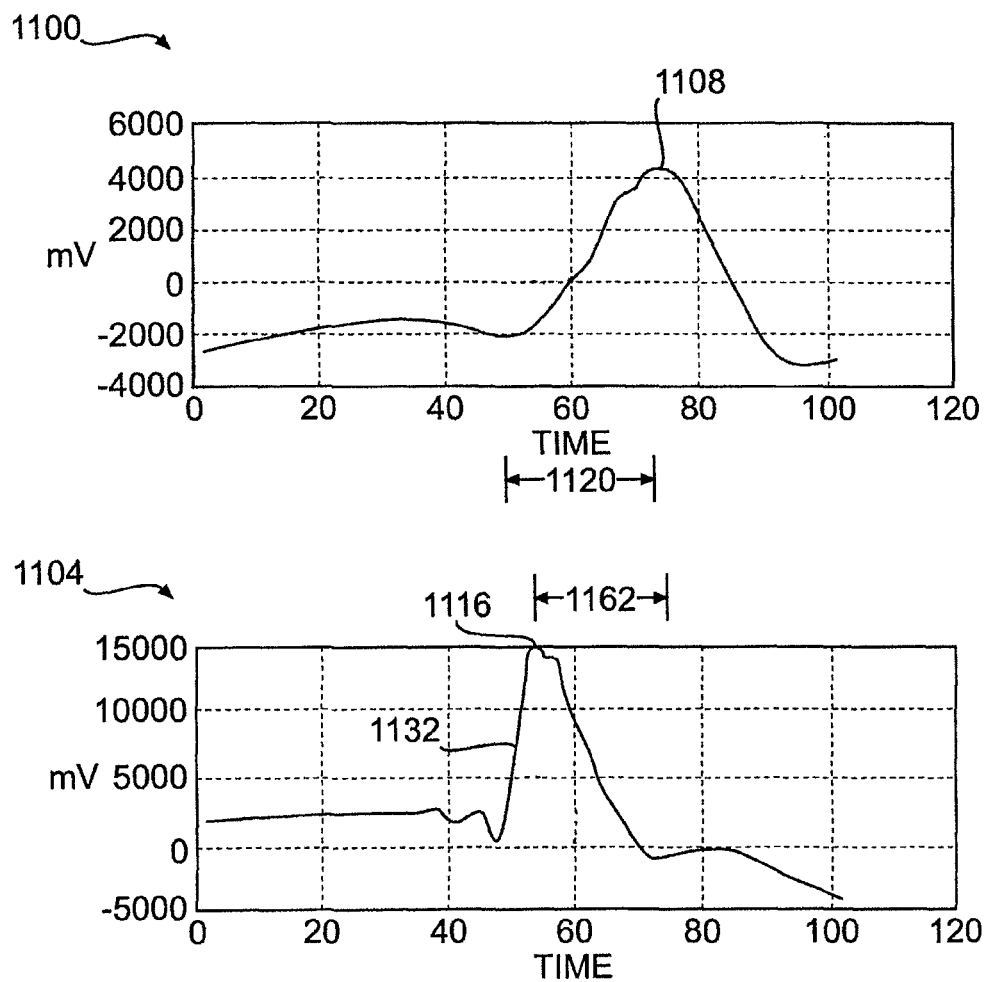
FIG. 11 illustrates a representative embodiment of a cardiac complex originating in a ventricular location, including an exemplary ventricular biologic pacemaker location.

Referring now to FIG. 11 there is shown an embodiment a cardiac complex originating in a biological pacemaker. FIG. 11 shows one embodiment of a first cardiac signal 1100 and a second cardiac signal 1104 of a QRS-cardiac complex originating in a biological pacemaker. The first cardiac signal 1100 is an example of a far-field cardiac signal, and the second cardiac signal 1104 is an example of a near-field cardiac signal sensed using the same electrodes used to sense the far-field cardiac signal of the first cardiac signal 1000 and the near-field signal of the second cardiac signal 1004.

In addition to using the same electrodes to sense the cardiac signals, the same selection criterion that were used in determining the timing template and the feature template for the normal sinus rhythm complexes are also used for subsequently-sensed cardiac complexes. In one embodiment, the selection criterion is the maximum point of the QRS-cardiac complex. FIG. 11 shows the maximum deflection point of the cardiac signal at approximately 1108 for the first cardiac signal 1100 and 1116 for the second cardiac signal 1104. In one embodiment, a time difference 1162 is determined between the maximum deflection point 1108 for the first cardiac signal and the maximum deflection point 1116 for the second cardiac signal. In an additional embodiment, a fiducial point 1132 is shown on the second cardiac signal 1104, where the timing difference 1120 between the first cardiac signal 1100 and the second cardiac signal 1104 is taken between the fiducial point 1132 and the maximum deflection point 1108 along the first cardiac signal 1104.

After making a determination as to whether a cardiac complex is a biological pacemaker complex or a complex originating in another cardiac location, a percentage of biological pacemaker complexes is determined at 950. At 960, the calculated percentage of the biological pacemaker complexes is compared to a predetermined percentage threshold. The comparison may be used, at 970, to adjust pacemaker or pharmaceutical therapy, or to evaluate the performance of the implanted biological pacemaker, as described further below.

As noted previously, some biological pacemakers may not begin to function as desired until some time after implantation. Further, biological pacemakers may be subject to the same potentially damaging conditions that affect any myocardial tissues (e.g. ischemia, apoptosis, etc). Therefore, it may be desirable to periodically or continuously monitor the function/performance of implanted biological pacemakers to determine if the biological pacemaker has begun functioning properly during an initial period after implantation and/or to determine if the biological pacemaker continues to function properly after more chronic use.

In some embodiments, as in a hospital or other inpatient setting, a patient's cardiac depolarizations may be continuously or periodically monitored using the systems and methods described previously. The cardiac signals may be transmitted to a central monitoring/recording system, as may be found at a nurse's station telemetry system. Alternatively, the signals may be stored for periodic review by a physician or other suitably-trained personnel. The signal may be transmitted using a wireless telemetry system attached to an implantable pacemaker or an external monitoring system.

To evaluate the performance of recently-implanted biological pacemakers, it may be necessary to vary the operation of an implanted pacemaker. For example, if an implanted pacemaker has a lower rate limit that exceeds the pacing rate of a recently-implanted biologic pacemaker, it may be difficult or impossible to determine if the biological pacemaker is functioning at all. Therefore, a physician may periodically instruct the implanted biological pacemaker to switch to a lower pacing rate or to cease pacing for a short time. Further, in some embodiments, the implantable pacemaker may be configured to periodically decrease the lower rate limit or cease pacing automatically for a short time. During this period, the pacemaker will continue to monitor and/or record cardiac depolarizations and to determine if sensed cardiac signals originate in an implanted biological pacemaker site or another cardiac location. Further, in some embodiments, the biological pacemaker may begin to pace at a rate greater than or approximately equal to the lower rate of the implanted pacemaker. In these situations, combinations of cardiac signals originating from the implantable device and the biological pacemaker may be sensed. Further, the implantable device may be configured to determine a percentage of signals originating in the biological pacemaker and/or to switch off or otherwise alter the pacing function of the implantable pacemaker if the biological pacemaker rate reaches a threshold level.

As noted previously, an implantable device may be configured to transmit information related to the function of a biological pacemaker and/or other cardiac performance characteristics to an external monitoring system. For example, such systems may include a variety of suitable automated patient management systems. A physician or other health care professional may monitor a patient from a remote site using such systems. Further, such systems may be configured to alert health care teams to changes in performance of a biologic pacemaker, an implantable device, or to potentially serious cardiac conditions such as arrhythmias or decreased cardiac output.

The invention claimed is:

1. An implantable medical device for monitoring an implantable biological cardiac pacemaker implanted in a heart, the device comprising:
   a first sensing system for detecting a first cardiac signal at a first location in the heart wherein the first cardiac signal is a near-field signal;
   a second sensing system for detecting a second cardiac signal at a second location in the heart wherein the second cardiac signal is a far-field signal; and
   a processor unit configured to compare information derived from the first cardiac signal and the second cardiac signal with at least one template cardiac signal indicative of a specific location of the implantable biological pacemaker within a heart and to determine if a cardiac depolarization from one location originated in a location of the implantable biological cardiac pacemaker or in a second location near the implantable biological cardiac pacemaker based on the information derived from the first cardiac signal and the second cardiac signal, the second location selected from the group consisting of a pacing lead site, a native pacemaker site, and an ectopic site.

2. The device of claim 1, further including at least one pacing lead configured to provide cardiac stimulating pulses for pacing the heart.

3. The device of claim 2, wherein the device is configured to provide cardiac pacing with a predetermined lower rate limit and to periodically decrease the lower rate limit to evaluate pacing by the implantable biological cardiac pacemaker.

4. The device of claim 3, wherein the decrease in the lower rate limit occurs at predetermined intervals.

5. The device of claim 3, wherein the decrease in the lower rate limit is initiated by a patient or physician.

6. The device of claim 1, further including at least one defibrillation circuit configured to provide cardiac defibrillation or cardioverting shocks.

7. The device of claim 1, further including at least one pacing lead and pacing circuit configured to provide cardiac resynchronization therapy.

8. The device of claim 1, further comprising:
   a template generator circuit coupled to at least one of the first sensing system and the second sensing system, wherein the template generator circuit determines a first normal sinus rhythm (NSR) representative complex and a second NSR representative complex from a plurality of cardiac complexes sensed during normal sinus rhythm;
   a morphology analyzer circuit coupled to the first sensing system, where the morphology analyzer circuit locates a predetermined feature in a cardiac complex detected in the first cardiac signal and in the first NSR representative complex, wherein the predetermined feature includes a repeatedly identifiable complex section common to the cardiac complex detected in the first cardiac signal and the first NSR representative complex; and
   a signal feature comparison circuit coupled to the morphology analyzer circuit and the template generator circuit, wherein the signal feature comparison circuit aligns the predetermined feature in the cardiac complex monitored in the first cardiac signal with the predetermined feature in the first NSR representative complex and compares the cardiac complex monitored in the second cardiac signal to the second NSR representative complex to determine whether the cardiac complex originated in a ventricular biological pacemaker complex.

9. The device of claim 1, further comprising:
   a morphology analyzer circuit coupled to at least one of the first sensing system and the second sensing system, wherein the morphology analyzer circuit locates a position of at least one predetermined feature in a morphology of a cardiac complex in the first cardiac signal and the second cardiac signal and generates two or more scalar values as a function of the position of the at least one predetermined feature for each of the first cardiac signal and the second cardiac signal;
   a template generator circuit coupled to the morphology analyzer circuit, wherein the template generator circuit creates a cardiac complex vector from the two or more scalar values generated by the morphology analyzer circuit; and
   a signal feature comparison circuit coupled to the morphology analyzer circuit and the template generator circuit, wherein the signal feature comparison circuit compares the cardiac complex vector to one or more classification vectors to determine if the a sensed cardiac complex originated in a ventricular biological pacemaker complex.

10. The device of claim 1, wherein the at least one template cardiac signal is produced by stimulating the location of the implantable biological cardiac pacemaker.

11. The device of claim 10, further comprising a stimulator lead for stimulating the location of the implantable biological cardiac pacemaker.

12. The device of claim 1, wherein the second sensing system includes an electrode positioned in a housing of the implantable device.

13. The device of claim 1, wherein the second sensing system includes at least one sense amplifier configured to pass an amplified signal to a morphology analyzer circuit.

14. The device of claim 1, wherein the far-field signal is a morphology signal.

15. The device of claim 1, wherein the first sensing system includes a first channel and an electrode configured to detect the near-field signal, and wherein the second sensing system include a second channel and an electrode configured to detect the far-field signal.

* * * * *